United States Patent
Yamanaka et al.

[11] Patent Number: 5,532,354
[45] Date of Patent: Jul. 2, 1996

[54] INTERMEDIATES FOR CEPHEM COMPOUNDS

[75] Inventors: Hideaki Yamanaka, Hirakata; Yoshiki Yoshida, both of Suita; Jiro Goto, Suita; Takeshi Terasawa; Shinya Okuda, both of Ikeda; Kazuo Sakane, Kawanishi, all of Japan

[73] Assignee: Fujisawa Pharmaceutical Co., Ltd., Osaka, Japan

[21] Appl. No.: 350,065

[22] Filed: Nov. 29, 1994

Related U.S. Application Data

[62] Division of Ser. No. 63,982, May 20, 1993, Pat. No. 5,401,734, which is a division of Ser. No. 885,252, May 20, 1992, Pat. No. 5,244,890, which is a continuation of Ser. No. 354,228, May 19, 1989, abandoned.

[30] Foreign Application Priority Data

Jun. 6, 1988 [GB] United Kingdom ............... 8813308
Jun. 15, 1988 [GB] United Kingdom ............... 8814196
Nov. 1, 1988 [GB] United Kingdom ............... 8825518

[51] Int. Cl.⁶ .................................. C07D 501/18
[52] U.S. Cl. .................................. 540/225; 540/222
[58] Field of Search .................... 540/227, 222, 540/225; 514/203

[56] References Cited

U.S. PATENT DOCUMENTS 5,244,890 9/1993 Yamanaka et al. ............... 540/222
5,254,679 10/1993 Bradbury et al. ............... 540/221

*Primary Examiner*—Nicholas Rizzo
*Attorney, Agent, or Firm*—Oblon, Spivak, McClelland, Maier & Neustadt

[57] ABSTRACT

Compounds of the formula:

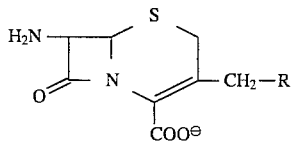

wherein R is a group of the formula:

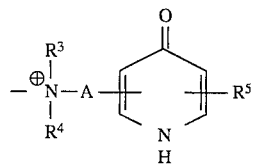

in which $R^3$ and $R^4$ are each lower alkyl or $R^3$ and $R^4$ are linked together to form $C_3$–$C_6$ alkylene, A is lower alkylene, and $R^5$ is hydroxy or a protected hydroxy group;

or a group of the formula:

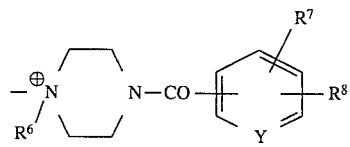

in which $R^6$ is lower alkyl, $R^7$ and $R^8$ are each hydroxy or a protected hydroxy group, and Y is N or CH, and salts thereof are intermediates for cephem compounds which show antimicrobial activities and which are useful in the treatment of microbial infections.

8 Claims, No Drawings

INTERMEDIATES FOR CEPHEM COMPOUNDS

The present invention is a divisional of application Ser. No. 08/063,982, filed May 20, 1993, now U.S. Pat. No. 5,401,734, which is a divisional of application Ser. No. 07/885,252, filed May 20, 1992, now U.S. Pat. No. 5,244,890, which is a continuation of application Ser. No. 07/354,228, filed May 19, 1989, abandoned.

The present invention relates to new cephem compounds and pharmaceutically acceptable salts thereof. More particularly, it relates to new cephem compounds and pharmaceutically acceptable salts thereof, which have antimicrobial activities, to processes preparation thereof, to pharmaceutical composition comprising the same, and to a method for treating infectious diseases in human being and animals.

Accordingly, one object of the present invention is to provide the cephem compounds and pharmaceutically acceptable salts thereof, which are highly active against a number of pathogenic microorganisms.

Another object of the present invention is to provide processes for the preparation of the cephem compounds and salts thereof.

A further object of the present invention is to provide pharmaceutical composition comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

The object cephem compounds are novel and can be represented by the following general formula (I):

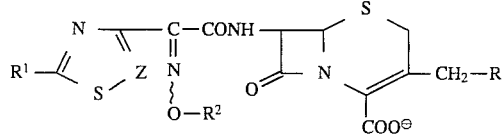

wherein $R^1$ is amino or a protected amino group,

Z is N or CH, $R^2$ is an organic group, and

R is a group of the formula:

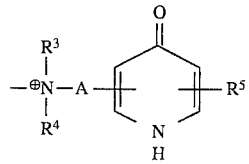

(in which $R^3$ and $R^4$ are each lower alkyl, or $R^3$ and $R^4$ are linked together to form $C_3$–$C_6$ alkylene, A is lower alkylene, and $R^5$ is hydroxy or a protected hydroxy group)

or a group of the formula:

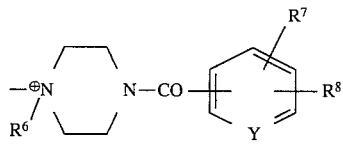

(in which $R^6$ is lower alkyl, $R^7$ and $R^8$ are each hydroxy or a protected hydroxy group, and Y is N or CH), The cephem compound (I) of the present invention can be prepared by processes as illustrated in the following, Process 1

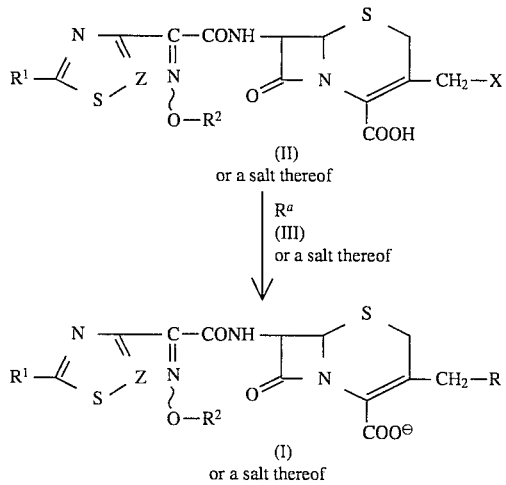

Process 2

-continued
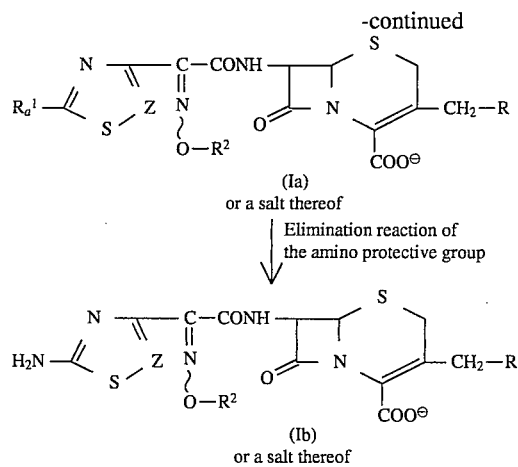
(Ia)
or a salt thereof
↓ Elimination reaction of the amino protective group
(Ib)
or a salt thereof
Process 3
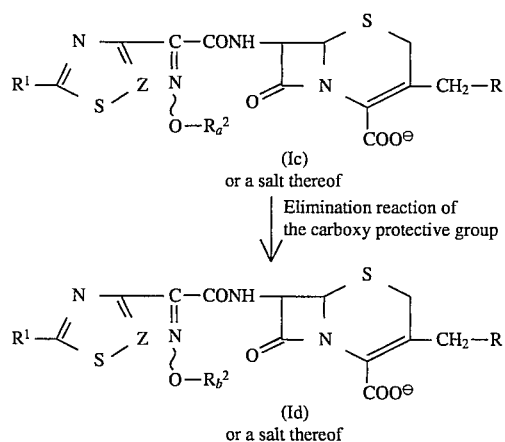
(Ic)
or a salt thereof
↓ Elimination reaction of the carboxy protective group
(Id)
or a salt thereof
Process 4
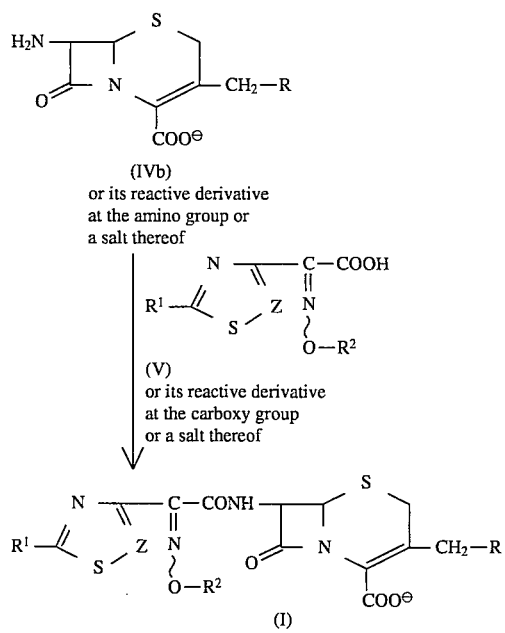
(IVb)
or its reactive derivative
at the amino group or
a salt thereof
(V)
or its reactive derivative
at the carboxy group
or a salt thereof
(I)
Process 5

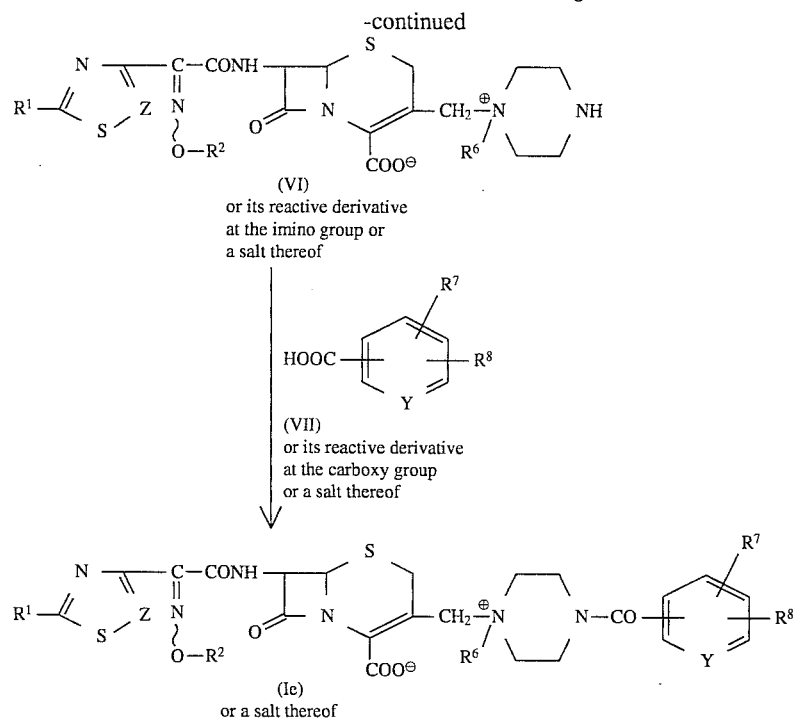

(Ic) or a salt thereof

Process 6

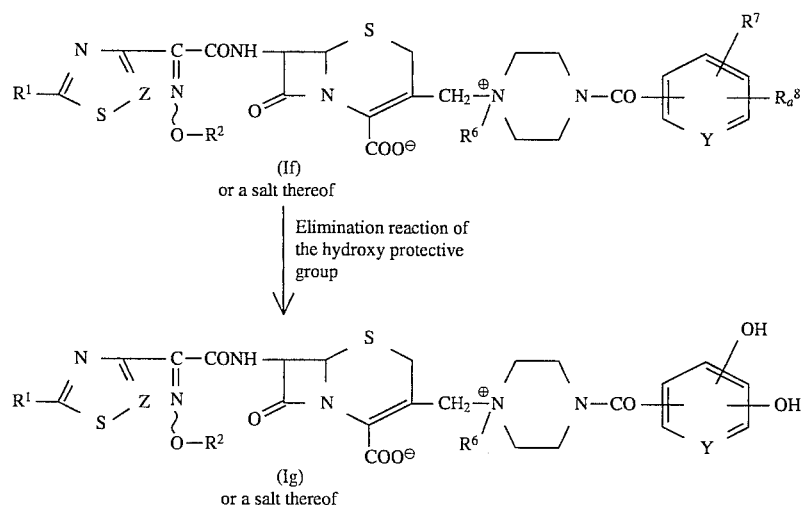

(Ig) or a salt thereof wherein R, $R^1$, $R^2$, $R^6$, $R^7$, $R^8$, Z and Y are each as defined above,
X is an acid residue,
$R^a$ is a compound of the formula:

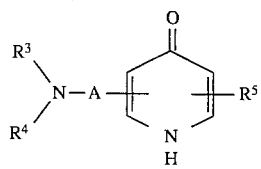

(in which $R^3$, $R^4$, $R^5$ and A are each as defined above)
or a compound of the formula:

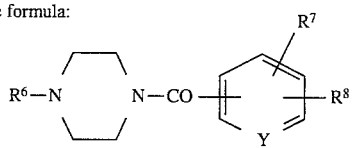

(in which $R^6$, $R^7$, $R^8$ and Y are each as defined above),
$R_a^1$ is a protected amino group,
$R_a^2$ is protected carboxy(lower)alkyl,
$R_b^2$ is carboxy(lower)alkyl, and $R_a^8$ is a protected hydroxy group.

Some of the starting compounds are novel and can be prepared by processes as illustrated in the following.

Process A

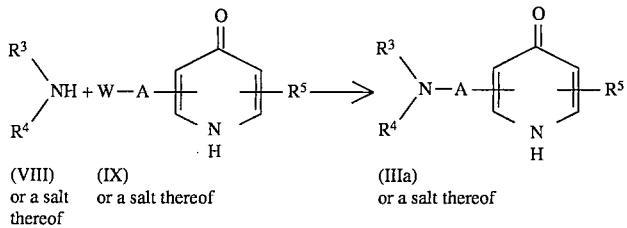

(VIII)  (IX)  (IIIa)
or a salt  or a salt thereof  or a salt thereof
thereof

Process B

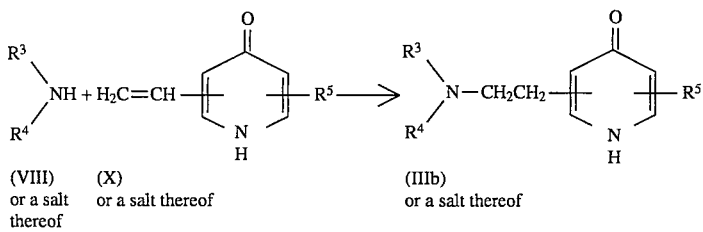

(VIII)  (X)  (IIIb)
or a salt  or a salt thereof  or a salt thereof
thereof

Process C

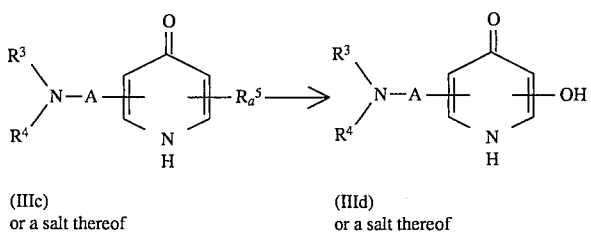

(IIIc)  (IIId)
or a salt thereof  or a salt thereof

Process D

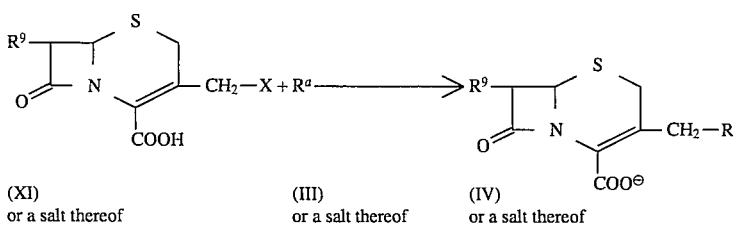

(XI)  (III)  (IV)
or a salt thereof  or a salt thereof  or a salt thereof

Process E

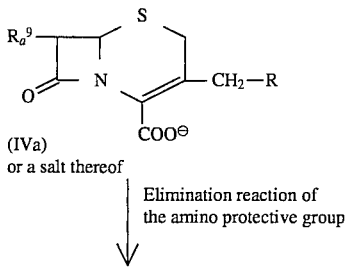

(IVa)
or a salt thereof

| Elimination reaction of the amino protective group

↓

-continued

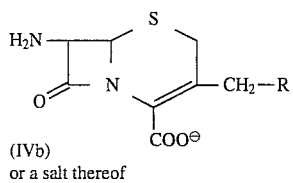

(IVb) or a salt thereof

Process F

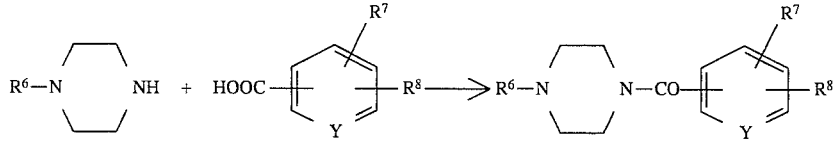

(XII)
or its reactive derivative
at the imino group
or a salt thereof (VII)
or its reactive derivative
at the carboxy group
or a salt thereof (IIIe)
or a salt thereof Process G

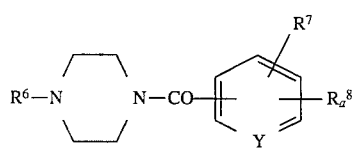

(IIIf) or a salt thereof

↓ Elimination reaction of the hydroxy protective group

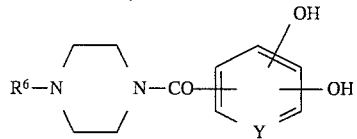

(IIIg) or a salt thereof

Process H

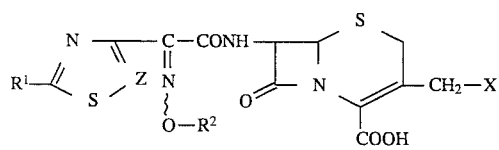

(II) or a salt thereof

① | $R^6-N\phantom{XX}N-R^{10}$

↓ (XIII)

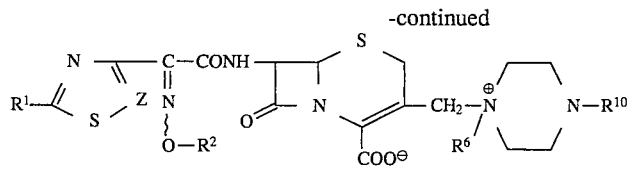

(XIV)
or a salt thereof

② | Elimination reaction of the imino protective group

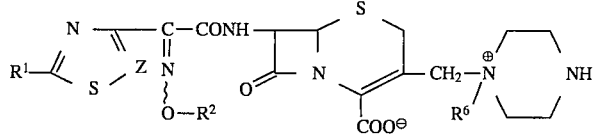

(VI)
or a salt thereof wherein $R^1, R^2, R^3, R^4, R^5, R^6, R^7, R^8, R_a^8, A, X, Y, Z, R$ and $R^a$ are each as defined above, W is an acid residue, $R_a^5$ is a protected hydroxy group, $R^9$ is amino or a protected amino group, $R_a^9$ is a protected amino group, and $R^{10}$ is an imino protective group.

Regarding the compounds (I), (Ia)–(Ig), (II), (V), (VI) and (XIV), it is to be understood that said compounds include syn isomer, anti isomer and a mixture thereof.

For example, with regard to the object compounds (I), syn isomer means one geometrical isomer having the partial structure represented by the following formula:

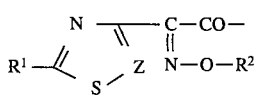

(wherein $R^1$, $R^2$ and Z are each as defined above) and anti isomer means the other geometrical isomer having the partial structure represented by the following formula:

$$R^1-\!\!\!\!\bigg\langle\!\!\begin{array}{c}N\\S\end{array}\!\!\!\!\bigg\rangle\!\!-Z\ \ \begin{array}{c}C-CO-\\ \|\\ R^2-O-N\end{array}$$

(wherein $R^1$, $R^2$ and Z are each as defined above) and all of such geometrical isomers and mixture thereof are included within the scope of this invention.

In the present specification and claim, the partial structure of these geometrical isomers and mixture thereof are represented for convenient sake by the following formula:

$$R^1-\!\!\!\!\bigg\langle\!\!\begin{array}{c}N\\S\end{array}\!\!\!\!\bigg\rangle\!\!-Z\ \ \begin{array}{c}C-CO-\\ \|\\ N\\ \{\\ O-R^2\end{array}$$

(wherein $R^1$, $R^2$ and Z are each as defined above).

Further, regarding the compounds (I), (Ia)–(Ig), (III), (IIIe), (IIIf), (IIIg), (IV), (IVa), (IVb) and (VII), it is to be understood that the said compounds include tautomeric isomers. For example, with regard to the object compound (I), in case that the symbol "R" in the compound (I) means the group represented by the following formula:

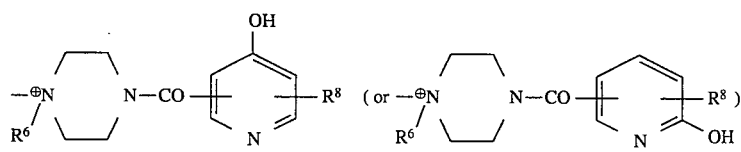

(wherein $R^6$ and $R^8$ are each as defined above), said group can also exist in the tautomeric form and such tautomeric equilibrium can be represented by the following scheme.

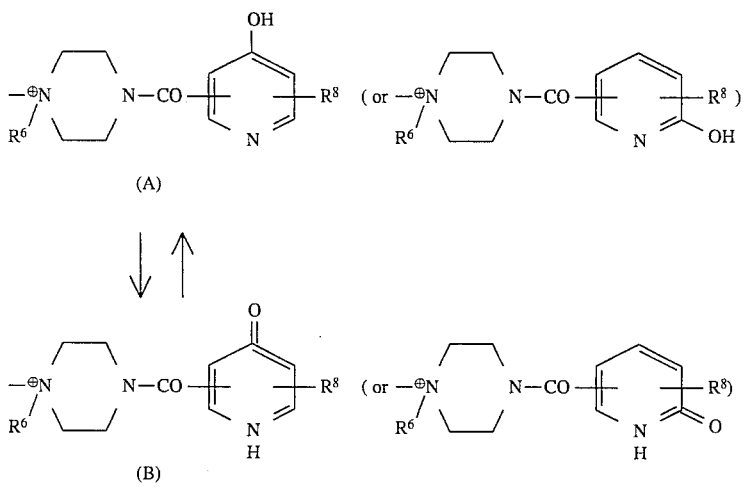

(A)

(B)

Both of the above tautomeric isomers are included within the scope of the present invention. In the present specification and claim, the compounds including the group of such tautomeric isomers are represented for the convenient sake by one expression of the group of the formula (A).

Still further, regarding the compounds (I), (Ia)–(Id), (III), (IIIa), (IIIb), (IIIc), (IIId), (IV), (IVa), (IVb), (IX) and (X), it is to be understood that the said compounds include tautomeric isomers. For example, with regard to the object compound (I), in case that the symbol "R" in the compound (I) means the group represented by the following formula:

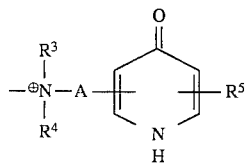

(wherein $R^3$, $R^4$, $R^5$ and A are each as defined above) said group can also exist in the tautomeric form and such tautomeric equilibrium can be represented by the following scheme.

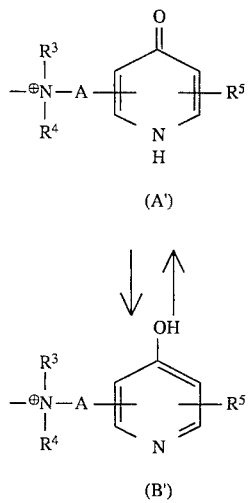

(A')

(B')

Both of the above tautomeric isomers are included within the scope of the present invention. In the present specification and claim, the compounds including the group of such tautomeric isomers are represented for the convenient sake by one expression of the group of the formula (A').

In the above and subsequent descriptions of the present specification, suitable examples and illustration of the various definitions which the present invention include within the scope thereof are explained in detail as follows.

The term "lower" is intended to mean 1 to 6 carbon atom(s) unless otherwise indicated.

Suitable "protected amino" may include an acylamino or an amino group substituted by a conventional protecting group such as ar(lower)alkyl which may have suitable substituent(s) (e.g. benzyl, trityl, etc.) or the like.

Suitable "acyl moiety" in the term "acylamino" may include carbamoyl, aliphatic acyl group and acyl group containing an aromatic: or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbon 1, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like. The acyl moiety as stated above may have suitable substituent(s) such as halogen (e.g. chlorine, bromine, iodine or fluorine) or the like.

Suitable "organic group" may include lower alkyl (e.g., methyl, ethyl, propyl, isopropyl, butyl, isobutyl, tert-butyl, pentyl, neopentyl, tert-pentyl, hexyl, etc.), mono(or di or tri)halo(lower)alkyl (e.g. chloromethyl, dichloromethyl, trichloromethyl, bromomethyl, chloroethyl, dichloroethyl, trichloroethyl, fluoroethyl, trifluoroethyl, etc.), lower alkenyl (e.g., vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3 butynyl, 1 or 2 or 3 or 4-pentynyl, 1 or 2 or 3 or 4 or 5-hexynyl, etc.), aryl (e.g., phenyl, naphthyl, etc.), ar(lower)alkyl such as phenyl(lower)alkyl (e.g., benzyl, phenethyl, phenylpropyl, etc.), carboxy(lower)alkyl wherein lower alkyl moiety can be referred to the ones as exemplified above, protected carboxy(lower)alkyl wherein lower alkyl moiety can be referred to the ones as exemplified above and protected carboxy moiety can be referred to the ones as exemplified below, and the like.

Suitable "protected carboxy moiety" in the term "protected carboxy(lower)alkyl" may include esterified carboxy and the like. And suitable examples of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.); lower alkenyl ester (e.g., vinyl ester, allyl ester, etc.); lower alkynyl ester (e.g., ethynyl ester, propynyl ester, etc.); lower alkoxyalkyl ester (e.g., methoxymethyl ester, ethoxymethyl ester, isopropoxymethyl ester, 1-methoxyethyl ester, 1-ethoxyethyl ester, etc.); lower alkylthioalkyl ester (e.g., methylthiomethyl ester, ethylthiomethyl ester, ethylthioethyl ester, isopropylthiomethyl ester, etc.); mono(or di or tri)halo(lower)alkyl ester (e.g. 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.); lower alkanesulfonyl(lower)alkyl ester (e.g. mesylmethyl ester, 2-mesylethyl ester etc.); ar(lower)alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester; lower alkylthioester (e.g. methylthioester, ethylthioester, etc.) and the like.

Suitable "lower alkyl" can be referred to the ones as exemplified above.

Suitable "$C_3$–$C_6$ alkylene" may include trimethylene, tetramethylene, pentamethylene and hexamethylene.

Suitable "lower alkylene" may include methylene, ethylene, trimethylene, tetramethylene, pentamethylene, hexamethylene and the like.

Suitable "protective group" in the "protected hydroxy group" may include acyl as mentioned above, tetrahydropyranyl and the like.

Suitable "acid residue" may include halogen [e.g. chlorine, bromine, iodine, etc.], acyloxy such as sulfonyloxy [e.g. benzenesulfonyloxy, tosyloxy, mesyloxy, etc.], lower alkanoyloxy [e.g. acetyloxy, propionyloxy, etc.] or the like.

Suitable "imino protective group" may include lower alkoxycarbonyl [e.g., methoxycarbonyl, ethoxycarbonyl, propoxycarbonyl, isopropoxycarbonyl, butoxycarbonyl, tert-butoxycarbonyl, pentyloxycarbonyl, tert-pentyloxycarbonyl, hexyloxycarbonyl, etc.] and the like.

Suitable pharmaceutically acceptable salts of the object compound (I) are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc], an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, aspartic acid salt, glutamic acid salt, etc.], and the like.

Preferred embodiments of the object compound (I) are as follows.

$R^1$ is amino or acylamino (more preferably lower alkanoylamino),

Z is N or CH, $R^2$ is lower alkyl, lower alkenyl, carboxy(lower)alkyl or protected carboxy(lower)alkyl [more preferably esterified carboxy(lower)alkyl, most preferably lower alkoxycarbonyl(lower)alkyl], $R^3$ and $R^4$ are each lower alkyl, or $R^3$ and $R^4$ are linked together to form $C_3$–$C_6$ alkylene, A is lower alkylene (more preferably $C_1$–$C_3$ alkylene), $R^5$ is hydroxy, $R^6$ is lower alkyl, $R^7$ is hydroxy or acyloxy (more preferably lower alkanoyloxy), $R^8$ is hydroxy or acyloxy (more preferably lower alkanoyloxy), and Y is N or CH.

The processes for preparing the object and starting compounds of the present invention are explained in detail in the following.

Process 1

The compound (I) or a salt thereof can be prepared by reacting the compound (II) or a salt thereof with the compound (III) or a salt thereof.

Suitable salts of the compounds (II) and (III) can be referred to the ones as exemplified for the compound (I).

The present reaction may be carried out in a solvent such as water, phosphate buffer, acetone, chloroform, acetonitrile, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction. Among the solvents, hydrophilic solvents may be used in a mixture with water. The reaction temperature is not critical, and the reaction is usually carried out under cooling, at ambient temperature or under warming.

Process 2

The compound (Ib) or a salt thereof can be prepared by subjecting the compound (Ia) or a salt thereof to elimination reaction of the amino protective group.

Suitable salts of the compounds (Ia) and (Ib) can be referred to the ones as exemplified for the compound (I).

This reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely affect the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely affect the reaction such as water, methanol, ethanol, propanol, N, N-dimethylformamide, or a mixture thereof. Additionally, in case that the abovementioned acids to be used in chemical reduction are in liquid, they can also be used as a solvent, further, a suitable solvent to be used in catalytic reduction may be the abovementioned solvent, and other conventional solvent such as diethyl ether, dioxane, tetrahydrofuran, alcohol (e.g. methanol, ethanol, etc.), etc., or a mixture thereof.

The reaction temperature of this reduction is not critical and the reaction is usually carried out under cooling to warming.

Process 3

The compound (Id) or a salt thereof can be prepared by subjecting the compound (Ic) or a salt thereof to elimination reaction of the carboxy protective group.

Suitable salts of the compound (Ic) and (Id) can be referred to the ones as exemplified for the compound (I).

This elimination can be carried out in a similar manner to that of the aforementioned Process 2, and therefore the reagents to be used and the reaction conditions (e.g. solvent, reaction temperature, etc.) can be referred to those of the Process 2.

Process 4

The compound (I) or a salt thereof can be prepared by reacting the compound (IVb) or its reactive derivative at the amino group or a salt thereof with the compound (V) or its reactive derivative at the carboxy group or a salt thereof.

Suitable reactive derivative at the amino group of the compound (IVb) may include Schiff's base type imino or its tautomeric enamine type isomer formed by the reaction of the compound (IVb) with a carbonyl compound such as aldehyde, ketone or the like; a silyl derivative formed by the reaction of the compound (IVb) with a silyl compound such as bis (trimethylsilyl)acetamide, mono (trimethylsilyl)acetamide [e.g. N-(trimethylsilyl)acetamide], bis (trimethylsilyl) urea or the like; a derivative formed by reaction of the compound (IVb) with phosphorus trichloride or phosgene, and the like.

Suitable salts of the compound (IVb) and its reactive derivative can be referred to the ones as exemplified for the compound (I).

Suitable reactive derivative at the carboxy group of the compound (V) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2^+$N=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H) -pyridone, N-hydroxysuccinimide, N-hydroxyphthalimide, 1-hydroxy-1H-benzotriazole, etc.], and the like. These reactive derivatives can optionally be selected from them according to the kind of the compound (V) to be used.

Suitable salts of the compound (V) and its reactive derivative can be referred to the ones as exemplified for the compound (I).

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (V) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro- 1H-benzotriazole; so-called Vilsmeier reagent prepared by the reaction of N,N-dimethylformamide with thionyl chloride, phosgene, trichloromethylchloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 5

The compound (Ie) or a salt thereof can be prepared by reacting the compound (VI) or its reactive derivative at the imino group or a salt thereof with the compound (VII) or its reactive derivative at the carboxy group or a salt thereof.

Suitable reactive derivative at the imino group of the compound (VI) may include a silyl derivative formed by the reaction of the compound (VI) with a silyl compound (e.g., N,O-bis(trimethylsilyl)acetamide, N-trimethylsilylacetamide, etc.); and the like.

Suitable salts of the compound (VI) and (VII) can be referred to the ones as exemplified for the compound (I).

Suitable reactive derivative at the carboxy group of the compound (VII) may include an acid halide, an acid anhydride, an activated amide, an activated ester, and the like.

This reaction can be carried out in a similar manner to that of the aforementioned Process 4, and therefore the reagents to be used and the reaction conditions (e.g. solvent, reaction temperature, etc.) can be referred to those of the Process 4.

Process 6

The compound (Ig) or a salt thereof can be prepared by subjecting the compound (If) or a salt thereof to elimination reaction of the hydroxy protective group.

Suitable salts of the compounds (If) and (Ig) can be referred to the ones as exemplified for the compound (I).

This elimination can be carried out in a similar manner to that of the aforementioned Process 2, and therefore the reagents to be used and the reaction conditions (e.g. solvent, reaction temperature, etc.) can be referred to those of the Process 2.

Process A

The compound (IIIa) or a salt thereof can be prepared by reacting the compound (VIII) or a salt thereof with the compound (IX) or a salt thereof.

The present reaction is usually carried out in the presence of a base.

Suitable base can be referred to the ones as exemplified in Process 2.

The reaction is usually carried out in a solvent such as water, an alcohol [e.g. methanol, ethanol, etc.], methylene chloride, tetrahydrofuran, a mixture thereof or any other solvent which does not adversely affect the reaction. The reaction temperature is not critical and the reaction is usually carried out under cooling to warming.

Process B

The compound (IIIb) or a salt thereof can be prepared by reacting the compound (VIII) or a salt thereof with the compound (X) or a salt. thereof.

The reaction is usually carried out in the presence or absence of a solvent such as water, an alcohol [e.g. methanol, ethanol, etc.], methylene chloride, tetrahydrofuran, a mixture thereof or any other solvent which does not adversely affect the reaction. The reaction temperature is not critical and the reaction is usually carried out under warming to heating.

Process C

The compound (IIId) or a salt thereof can be prepared by subjecting the compound (IIIc) or a salt thereof to elimination reaction of the hydroxy protective group.

The elimination reaction can be carried out in a similar manner to that of the aforementioned Process 2, and therefore the reagents to be used and the reaction conditions (e.g. solvent, reaction temperature, etc.) can be referred to those of the Process 2.

Process D

The compound (IV) or a salt thereof can be prepared by reacting the compound (XI) or a salt thereof with the compound (III) or a salt thereof.

This reaction can be carried out in a similar manner to that of the aforementioned Process 1, and therefore the reagents to be used and the reaction conditions (e.g. solvent, reaction temperature, etc.) can be referred to those of the Process 1.

Process E

The compound (IVb) or a salt thereof can be prepared by subjecting the compound (IVa) or a salt thereof to elimination reaction of the amino protective group.

This elimination can be carried out in a similar manner to that of the aforementioned Process 2, and therefore the reagents to be used and the reaction conditions (e.g. solvent, reaction temperature, etc.) can be referred to those of the Process 2.

Process F

The compound (IIIe) or a salt thereof can be prepared by reacting the compound (XII) or its reactive derivative at the imino group or a salt thereof with the compound (VII) or its reactive derivative at the carboxy group or a salt thereof.

Suitable reactive derivative at the imino group of the compound (XII) may include the same one as exemplified for the compound (VI) in Process 5.

The present reaction can be carried out in a similar manner to that of the aforementioned Process 4, and therefore the reagents to be used and the reaction conditions (e.g. solvent, reaction temperature, etc.) can be referred to those of the Process 4.

Process G

The compound (IIIg) or a salt thereof can be prepared by subjecting the compound (IIIf) or a salt thereof to elimination reaction of the hydroxy protective group.

This elimination reaction can be carried out in a similar manner to that of the aforementioned Process 2, and therefore the reagents to be used and the reaction conditions (e.g. solvent, reaction temperature, etc.) can be referred to those of the Process 2.

Process H—①

The compound (XIV) or a salt thereof can be prepared by reacting the compound (II) or a salt thereof with the compound (XIII).

The present reaction can be carried out in a similar manner to that of the aforementioned Process 1, and therefore the reagent to be used and the reaction conditions (e.g. solvent, reaction temperature, etc.) can be referred to those of the Process 1.

Process H—②

The compound (VI) or a salt thereof can be prepared by subjecting the compound (XIV) or a salt thereof to elimination reaction of the imino protective group.

This elimination can be carried out in a similar manner to that of the aforementioned Process 2, and therefore the reagents to be used and the reaction conditions (e.g. solvent, reaction temperature, etc.) can be referred to those of the Process 2.

The object compound (I) and pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compound (I), the test data on MIC (minimal inhibitory concentration) of representative compound of this invention are shown in the following.

Test method:

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar)containing graded concentrations of representative test compound, and the minimal inhibitory concentration (MIC) was expressed in terms of μg/ml after incubation at 37° C. for 20 hours.

Test compound:
(1) 7β-[2-(5-Amino-1,2,4-thiadiazol-3-yl)-2-(1-carboxy-1-methylethoxyimino)acetamido]-3-[N,N-dimethyl-N-{(5 -hydroxy-4-oxo-1,4-dihydropyridin-2-yl)methyl}ammonio]methyl-3-cephem-4-carboxylate (syn isomer)

(2) 7β-[2-(5-Amino-1,2,4-thiadiazol-3-yl)-2-methoxyiminoacetamido]-3-[1-methyl-4-(4,5-dihydroxy- 2-pyridylcarbonyl)-1-piperazinio]methyl-3-cephem-4-carboxylate (syn isomer)

| | Test result MIC (μg/ml) | |
|---|---|---|
| | Test compounds | |
| Test strain | (1) | (2) |
| P. aeruginosa 26 | ≦0.025 | 0.05 |

For therapeutic administration, the object compound (I) and pharmaceutically acceptable salts thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration.

The pharmaceutical preparations may be in solid form such as tablet, granule, powder, capsule, or liquid form such as solution, suspension, syrup, emulsion, lemonade and the like.

If needed, there may be included in the above preparations, auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases, a kind of the compound (I) to be applied, etc., in general, amounts between 1 mg and about 4,000 mg or even more per day may be administered to a patient. An average single dose of about 50 mg, 100 mg, 250 mg, 500 mg, 1000 mg of the object compound (I) of the present invention may be used in treating diseases infected by pathogenic microorganisms.

The following Preparations and Examples are given for the purpose of illustrating the present invention in more detail.

Preparation 1

To a mixture of 2-chloromethyl-5-benzyloxy-4-pyridone (1.0 g), tetrahydrofuran (10 ml) and water (10 ml) were added dimethylamine hydrochloride (1.31 g) and sodium hydroxide (0.64 g). After being stirred for 1.5 hours, the mixture was concentrated under reduced pressure to dryness. The residue was dissolved in methanol and the insoluble material was filtered off. The filtrate was evaporated in vacuo to give 5-benzyloxy- 2-(N,N-dimethylamino)methyl-4-pyridone (1.0 g) as a powder.

IR (Nujol): 1620 cm$^{-1}$

NMR (DMSO-d$_6$, δ): 2.20 (6H, s), 3.36 (2H, s), 5.06 (2H, s), 6.28 (1H, s), 7.1 (5H, m), 7.13 (1H, s).

Preparation 2

A solution of 5-benzyloxy-2-chloromethyl-4-pyridone (10.0 g) and triphenylphosphine (10.5 g) in N,N-dimethylformamide (50 ml) was stirred for 5 hours at 90°–100° C. The resulting mixture was poured into ethyl acetate (800 ml). The precipitate was collected by filtration, washed with ethyl acetate and dissolved in dichloromethane (500 ml). To the solution were added water (300 ml) and 38% aqueous formaldehyde (100 ml). The mixture was adjusted to pH 10–10.5 with potassium carbonate. After being stirred for 3 hours at 35°–40° C., the organic layer was separated, washed with water, dried over magnesium sulfate and concentrated under reduced pressure. The product was isolated by column chromatography on silica gel with ethyl acetate as an eluent to give 5-benzyloxy-2-vinyl-4-pyridone (6.02 g).

IR (Nujol): 1640, 1615 cm$^{-1}$

NMR (DMSO-d$_6$, δ): 5.10 (2H, s), 5.46 (1H, d, J=10Hz), 5.95 (1H, d, J=18Hz), 6.57 (1H, s), 6.63 (1H, dd, J=10Hz, 18Hz), 7.43 (5H, m), 7.66 (1H, s).

Preparation 3

A mixture of 5-benzyloxy-2-vinyl-4-pyridone (2.90 g) and pyrrolidine (5.33 ml) was heated and refluxed for an hour. The mixture was cooled and diluted with tetrahydrofuran (20 ml) and diisopropyl ether (80 ml). After being stirred for an hour at ambient temperature, the resulting precipitate was collected by filtration, washed with diisopropyl ether and air-dried at ambient temperature to give 5-benzyloxy-2-[2-(1-pyrrolidinyl)ethyl]-4-pyridone (3.79 g).

IR (Nujol): 1633, 1618 cm$^{-1}$

NMR (DMSO-d$_6$, δ): 1.70 (4H, m), 2.3–2.7 (8H, m), 5.03 (2H, s), 6.15 (1H, s), 7.40 (5H, m), 7.41 (1H, s).

Preparation 4

A mixture of 5-benzyloxy-2-vinyl-4-pyridone (3.12 g), 50% aqueous solution of dimethylamine (15 ml) and ethanol (35 ml) was heated at 100° C. in a sealed tube for 8 hours. The resulting mixture was cooled and concentrated under reduced pressure to dryness. The residue was triturated with a mixture of ethyl acetate and diisopropyl ether to give 5-benzyloxy-2-[2-(N,N-dimethylamino) ethyl]-4-pyridone (3.45 g) as a powder.

IR (Nujol): 1620 (sh), 1613 cm$^{-1}$

NMR (DMSO-d$_6$, δ): 2.16 (6H, m), 2.55 (2H, m), 5.01 (2H, s), 6.13 (1H, s), 7.38 (5H, m), 7.40 (1H, s).

Preparation 5

(1) 5-Benzyloxy-2-(N,N-dimethylamino) methyl-4-pyridone 1.0 g) in methanol (15 ml) was subjected to catalytic reduction with 10% palladium on activated carbon (200 mg) at atmospheric pressure. After removal of catalyst, the solution was concentrated under reduced pressure to give 2-(N,N-dimethylamino) methyl -5-hydroxy-4-pyridone (0.96 g).

IR (Nujol): 3300 (br), 1620 cm$^{-1}$

NMR (DMSO-d$_6$, δ): 2.27 (6H, s), 3.43 (2H, s), 6.30 (1H, s), 7.40 (1H, s).

The following compounds were obtained according to a similar manner to that of Preparation 5(1).

(2) 5-Hydroxy-2-[2-(N,N-dimethylamino) ethyl]-4-pyridone

IR (Nujol): 1640 (sh), 1630 cm$^{-1}$

NMR (D$_2$O, δ): 2.50 (6H, m), 2.92 (2H, m), 6.48 (1H, s), 7.47 (1H, s).

(3) 5-Hydroxy-2-[2-(1-pyrrolidinyl)ethyl]-4-pyridone

IR (Nujol): 1623 (sh), 1608 cm$^{-1}$

NMR (D$_2$O, δ): 1.8–2.1 (4H, m), 2.7–3.3 (8H, m), 6.43 (1H, s), 7.36 (1H, s).

EXAMPLE 1

(1)

To a mixture of benzhydryl 7β-[2-(5-amino-1,2,4-thiadiazol- 3-yl)-2-methoxyiminoacetamido]-3-chloromethyl-3-cephem-4-carboxylate (syn isomer) (1.47 g), dichloromethane (5 ml) and anisole (1.4 ml) was added trifluoroacetic acid (5 ml) under ice-cooling with stirring. After being stirred for 30 minutes at the same temperature, the mixture was poured into diisopropyl ether (100 ml). The resulting precipitate was collected by filtration, washed with diisopropyl ether and dried under reduced pressure to give 7-[2-(5-amino-1,2,4-thiadiazol- 3-yl)-2-methoxyiminoacetamido]-3-chloromethyl- 3-cephem-4-carboxylic acid trifluoroacetate (syn isomer). This compound was dissolved in N,N-dimethylformamide (15 ml). To the solution was added 2-(N,N-dimethylamino)methyl- 5-hydroxy-4-pyridone (1.24 g). After being 10 stirred for 5 hours at ambient temperature, the reaction mixture was poured into ethyl acetate (100 ml). The resulting precipitate was collected by filtration, washed with ethyl acetate. The precipitate was suspended in water (100 ml) and the suspension was adjusted to pH 2.0 with diluted hydrochloric acid. After removal of insoluble material by filtration, the aqueous solution was subjected to column chromatography on Diaion HP-20 [Trademark: prepared by Mitsubishi Chemical Industries]. The column was washed with water and the elution was carried out with 30% aqueous methanol. The fractions containing desired product were combined and methanol was evaporated in vacuo. The resulting aqueous layer was lyophilized to give 7β-[2-(5-amino-1,2,4-thiadiazol- 3-yl)-2-methoxyiminoacetamido]-3-[N,N-dimethyl-N-{(5-hydroxy-4-oxo-1,4-dihydropyridin-2-yl)methyl}ammonio] methyl-3-cephem-4-carboxylate (syn isomer) (0.28 g) as a powder.

IR (Nujol): 3250 (br), 1765, 1650, 1600 cm$^{-1}$

NMR (D$_2$O-NaHCO$_3$, δ): 3.0 (3H, br.s), 3.07 (3H, br. s), 3.40, 3.71 (2H, ABq, J=17Hz), 3.85–4.9 (4H, m), 4.05 (3H, s), 5.33 (1H, d, J=5Hz), 5.85 (1H, d, J=5Hz), 6.73 (1H, s), 7.70 (1H, s).

The following compounds were obtained according to a similar manner to that of Example 1 (1).

(2) 7β-[2-(2-Formamidothiazol-4-yl)-2-tert-butoxycarbonylmethoxyiminoacetamido]-3-[N,N-dimethyl-N-{(5-hydroxy-4-oxo-1,4-dihydropyridin-2-yl)methyl}ammonio] methyl-3-cephem-4-carboxylate (syn isomer)

IR (Nujol): 3300 (br), 1780, 1730, 1675, 1613 cm$^{-1}$

NMR (D$_6$O-DCl, δ): 1.30 (9H, s), 3.3 (6H, m), 3.6–4.3 (2H, m), 4.6–5.2 (6H, m), 5.60 (1H, d, J=5Hz), 5.90 (1H, d, J=5Hz), 7.33 (1H, s), 7.70 (1H, s), 8.30 (1H, s), 8.41 (1H, s).

(3) 7β-[2-(2-Formamidothiazol-4-yl)-2-methoxyiminoacetamido]-3-[N,N-dimethyl-N-{2-(5-hydroxy-4-oxo-1,4 -dihydropyridin-2-yl)ethylammonio]methyl-3-cephem-4-carboxylate (syn isomer)

IR (Nujol) 3200 (br), 1772, 1670, 1608 cm$^{-1}$

NMR (D$_6$O-DCl, δ): 3.23 (3H, s), 3.30 (3H, s), 3.2–4. 5 (6H, m), 4.6–5.1 (2H, m), 5.43 (1H, d , J=5Hz ), 5.83 (1H, d, J=5Hz ), 7.58 (1H, s), 7.80 (1H, s), 8.07 (1H, s), 8.50 (1H, s).

EXAMPLE 2

(1)

To a solution of 7β-[2-(5-amino-1,2,4-thiadiazol-3-yl)-2-(1-carboxy-1-methylethoxyimino)acetamido]-3 -chloromethyl-3-cephem-4-carboxylic acid trifluoroacetate (syn isomer) (1.0 g) in-N,N-dimethylformamide (10 ml) was added 2-(N,N-dimethylamino) methyl-5-hydroxy-4-pyridone (.1.09 g). After being stirred for 5 hours at ambient temperature, the mixture was poured into ethyl acetate (150 ml). The resulting precipitate was collected by filtration, washed with ethyl acetate and dried under reduced pressure. The precipitate was suspended in water (50 ml) at pH 2.0 and stirred for 30 minutes. After removal of insoluble material, the aqueous solution was subjected to column chromatography on Diaion HP-20. The column was washed with water and the elution was carried out with 30% aqueous methanol. The fractions containing desired product was combined and methanol was evaporated in vacuo. The resulting aqueous layer was lyophilized to give 7β-[2-(5-amino- 1,2,4-thiadiazol-3-yl)-2-(1-carboxy-1-methylethoxyimino)acetamido]-3-[N,N-dimethyl-N-{(5-hydroxy-4-oxo-1,4 -dihydropyridin-2-yl)methyl}ammonio]methyl-3-cephem-4-carboxylate (syn isomer) (0.30 g) as a powder.

IR (Nujol): 3250 (br), 1770, 1670 (sh), 1600 cm$^{-1}$

NMR (D$_2$O-NaHCO$_3$, δ): 1.56 (6H, s), 3.03 (3H, br. s), 3.10 (3H, br s), 3.44, 3.96 (2H, ABq, J=18 Hz), 4.1–5.0 (4H, m), 5.37 (1H, d, J=5Hz), 5.88 (1H, d, J=5Hz), 6.76 (1H, s), 7.71 (1H, s).

The following compounds were obtained according to similar manner to that of Example 2(1).

(2) 7β-[2-(5-Amino-1,2,4-thiadiazol-3-yl)-2-methoxyiminoacetamido]-3-[1-{2-(5-hydroxy-4-oxo-1,4-dihydropyridin- 2-yl)ethyl}-1-pyrrolidinio]methyl =3-cephem-4-carboxylate (syn isomer)

IR (Nujol): 3300 (br), 1765, 1663 (sh), 1620 cm$^{-1}$

NMR (D$_2$O-NaHCO$_3$, δ): 2.05 (4H, m), 3.0–3.8 (10H, m), 4.07 (3H, s), 4.6–4.9 (2H, m), 5.18 (1H, d, J=5Hz), 5.80 (1H, d, J=5Hz), 6.45 (1H, s), 7.51 (1H, s).

(3) 7β-[2-(5-Amino-1,2,4-thiadiazol-3-yl)-2-(1-carboxy-1-methylethoxyimino)acetamido]-3-[1-{2-(5-hydroxy-4 -oxo-1,4-dihydropyridin-2-yl)ethyl}-1-pyrrolidinio]methyl-3-cephem-4-carboxylate (syn isomer)

IR (Nujol): 3300 (br), 1770, 1670–1620 (br) cm$^{-1}$

NMR (D$_2$O-NaHCO$_3$, δ): 1.53 (6H, s), 2.06 (4H, m), 3.0–3.8 (10H, m), 4.4–4.9 (2H, m), 5.10 (1H, d, J=5Hz), 5.80 (1H, d, J=5Hz), 6.43 (1H, s), 7.85 (1H, s).

(4) 7β-[2-(5-Amino-1,2,4-thiadiazol-3-yl)-2-(1-carboxy-1-methylethoxyimino)acetamido]-3-[N,N-dimethyl-N-{2-(5 -hydroxy-4-oxo-1,4-dihydropyridin-2-yl)ethyl}ammonio]methyl- 3-cephem-4-carboxylate (syn isomer)

IR (Nujol): 3300 (br), 1775, 1670, 16 15 cm$^{-1}$

NMR (D$_2$O-NaHCO$_3$, δ): 1.55 (6H, s), 3.00 (3H, br. s), 3.15 (3H, br. s), 3.2–4.2 (4H, m), 4.6–4.9 (2H, m), 5.35 (1H, d, J=5Hz), 5.80 (1H, d, J=5Hz), 6.45 (1H, s), 7.54 (1H, s).

(5) 7β-[2-(5-Amino-1,2,4-thiadiazol-3-yl)-2-methoxyiminoacetamido]-3-[N,N-dimethyl-N-{2-(5-hydroxy-4-oxo-1,4-dihydropyridin-2-yl)ethyl}ammonio]methyl-3-cephem- 4-carboxylate (syn isomer)

IR (Nujol): 3250 (br), 1770, 1670(sh), 1610 cm$^{-1}$

NMR (D$_2$O-NaHCO$_3$, δ): 3.06 (3H, br. s), 3.13 (3H, br. s), 3.2–4.2 (4H, m), 4.03 (3H, s), 4.6–4.9 (2H, m), 5.31 (1H, d, J=5Hz), 5.80 (1H, d, J=5Hz), 6.45 (1H, s), 7.50 (1H, s).

(6) 7β-[2-(2-Formamidothiazol-4-yl)-2-(1-tert-butoxycarbonyl- 1-methylethoxyimino)acetamido]-3-[N,N-dimethyl-N-{2-(5-hydroxy-4-oxo-1,4-dihydropyridin-2-yl)ethyl}ammonio]methyl-3-cephem-4-carboxylate (syn isomer)

IR (Nujol): 3200, 1770, 1720, 1685 (sh), 1668, 1605 cm$^{-1}$

NMR (D$_2$O-NaHCO$_3$, δ): 1.45 (9H, s), 1.55 (6H, s), 2.10 (3H, s), 3.16 (3H, s), 3.0–4.6 (6H, m), 4.5–4.9 (2H, m), 5.37 (1H, d, J=5Hz), 5.85 (1H, d, J=5Hz), 6.47 (1H, s), 7.45 (1H, s), 7.54 (1H, s), 8.50 (1H, s).

(7) 7β-[2-(2-Formamidothiazol-4-yl)-2-(1-tert-butoxycarbonyl- 1-methylethoxyimino)acetamido]-3-[N,N-dimethyl-N-{(5-hydroxy-4-oxo-1,4-dihydropyridin-2-yl)methyl}ammonio]methyl-3-cephem-4-carboxylate (syn isomer)

IR (Nujol): 3250, 1780, 1720, 1675, 1611 cm$^{-1}$

NMR (D$_6$O-DCl, δ): 1.35 (9H, s), 1.60 (6H, s), 3.30 (3H, s), 3.37 (3H, s), 3.6–4.6 (4H, m), 4.92 (2H, br.s), 5.53 (1H, d, J=5Hz), 5.90 (1H, d, J=5Hz), 7.28 (1H, s), 7.70 (1H, s), 8.30 (1H, s), 8.37 (1H, s).

(8) 7β-[2-(2-Aminothiazol-4-yl)-2-tert-butoxycarbonylmethoxyiminoacetamido]-3-[N,N-dimethyl-N-{(5-hydroxy-4 -oxo-1,4-dihydropyridin-2-yl)methyl}ammonio] methyl-3 -cephem-4-carboxylate (syn isomer)

IR (Nujol): 3300 (br.), 1750, 1730 (sh), 1667, 1608 cm$^{-1}$ (9) 7β-[2-(2-Aminothiazol-4-yl)-2-methoxyiminoacetamido]- 3-[N,N-dimethyl-N-{2-(5-hydroxy-4-oxo-1,4-dihydropyridin- 2-yl)ethyl}ammonio]methyl-3-cephem-4-carboxylate (syn isomer)

IR (Nujol): 3250 (br), 1770, 1660, 1705 cm$^{-1}$

(10) 7β-[2-(2-Aminothiazol-4-yl)-2-(1-tert-butoxycarbonyl-1-methylethoxyimino)acetamido]-3-[N,N-dimethyl-N-[2-(5-hydroxy-4-oxo-1,4-dihydropyridin-2-yl)ethyl}ammonio]methyl-3-cephem-4-carboxylate (syn isomer)

IR (Nujol): 3250 (br.), 1770, 1720, 1662, 1608 cm$^{-1}$

(11) 7β-[2-(2-Aminothiazol-4-yl)-2-(1-tert-butoxycarbonyl-1-methylethoxyimino)acetamido]-3-[N,N-dimethyl-N-{(5-hydroxy-4-oxo-1,4-dihydropyridin-2-yl)methyl}ammonio]methyl-3-cephem-4-carboxylate (syn isomer)

IR (Nujol): 3350 (br.), 1775, 1720, 1672, 1608 cm$^{-1}$

(12) 7β-[2-(2-Aminothiazol-4-yl)-2-carboxymethoxyiminoacetamido]-3-[N,N-dimethyl-N-{(5-hydroxy-4-oxo-1,4 -dihydropyridin-2-yl)methyl}ammonio]methyl-3-cephem-4-carboxylate (syn isomer)

IR (Nujol): 3250 (br), 1770, 1662 (sh), 1600 cm$^{-1}$

(13) 7β-[2-(2-Aminothiazol-4-yl)-2-(1-carboxy-1-methylethoxyimino)acetamido]-3-[N,N-dimethyl-N-{2-(5-hydroxy-4 -oxo-1,4-dihydropyridin-2-yl)ethyl}ammonio] methyl-3 -cephem-4-carboxylate (syn isomer)

IR (Nujol): 3250 (br), 1770, 1665, 1610 cm$^{-1}$

(14) 7β-[2-(2-Aminothiazol-4-yl)-2-(1-carboxy-1-methylethoxyimino)acetamido]-3-[N,N-dimethyl-N-{(5 -hydroxy-4-oxo-1,4-dihydropyridin-2-yl)methyl}ammonio]-methyl-3-cephem-4-carboxylate (syn isomer)

IR (Nujol): 3250, 1770, 1662, 1607 cm$^{-1}$

(15) 7β-[2-(5-Amino-1,2,4-thiadiazol-3-yl)-2-(1-carboxy-1 -methylethoxyimino)acetamido]-3-[N,N-dimethyl-N-{(5 -hydroxy-4-oxo-1,4-dihydropyridin-2-yl)methyl}ammonio]-methyl-3-cephem-4-carboxylate hydrochloride (syn isomer)

IR (Nujol): 3450–3150 (br), 2650, 1770, 1670, 1610 cm$^{-1}$

(16) Sulfuric acid salt of 7β-[2-(5-amino-1,2,4 -thiadiazol-3-yl)-2-(1-carboxy-1-methylethoxyimino)acetamido]-3-[N,N-dimethyl-N-{(5-hydroxy-4-oxo-1,4 -dihydropyridin-2-yl)methyl}ammonio]methyl-3-cephem-4-carboxylate (syn isomer)

IR (Nujol): 3450–3150 (br), 2650 (br), 1780, 1692, 1615, 1558, 1529 cm$^{-1}$

EXAMPLE 3

(1)

To a suspension of 7β-[2-(2-formamidothiazol-4-yl)-2-tert-butoxycarbonylmethoxyiminoacetamido]-3-[N,N-dimethyl-N-{(5-hydroxy-4-oxo-1,4-dihydropyridin-2-yl)methyl}ammonio]methyl-3-cephem-4-carboxylate (syn isomer) (0.70 g) in methanol (35 ml) was added conc. hydrochloric acid (0.53 ml). After being stirred at ambient temperature, the reaction mixture was diluted with water (50 ml) and methanol was evaporated under reduced pressure.

The resulting aqueous solution was adjusted to pH 1.0 and subjected to column chromatography on Diaion HP-20 (50 ml). The column was washed with water and the elution was carried out with 40% aqueous isopropanol. The fractions containing the object compound was lyophilized to give 7β-[2-(2-aminothiazol-4-yl)-2-tert-butoxycarbonylmethoxyiminoacetamido]-3-[N,N-dimethyl-N-{(5-hydroxy-4 -oxo-1,4-dihydropyridin-2-yl)methyl} ammonio]methyl-3-cephem-4-carboxyl ate (syn isomer) (0.53 g).

IR (Nujol): 3300 (br), 1750, 1730 (sh), 1667, 1608 cm$^{-1}$
NMR (D$_2$O-NaHCO$_3$, δ): 1.50 (9H, s), 2.97 (3H, br.s), 3.06 (3H, br. s), 3.2–4.2 (4H, m), 4.36 (2H, br. s), 4.65 (2H, s), 5.35 (1H, d, J=5Hz), 5.86 (1H, d, J=5Hz), 6.73 (1H, s), 7.00 (1H, s), 7.73 (1H, s).

The following compounds were obtained according to similar manner to that of Example 3(1).

(2) 7β-[2-(2-Aminothiazol-4-yl)-2-methoxyiminoacetamido]- 3-[N,N-dimethyl-N-{2-(5-hydroxy-4-oxo-1,4-dihydropyridin- 2-yl)ethyl}ammonio]methyl-3-cephem-4-carboxylate (syn isomer)

IR (Nujol): 3250 (br), 1770, 1660, 1705 cm$^{-1}$
NMR (D$_2$O-NaHCO$_3$, δ): 3.10 (3H, s), 3.15 (3H, s), 3.0–4.2 (6H, m), 4.5–4.9 (2H, m), 5.33 (1H, d, J=5Hz), 5.80 (1H, d, J=5Hz), 6.50 (1H, s), 6.95 (1H, s), 7.51 (1H, s).

(3) 7β-[2-(2-Aminothiazol-4-yl)-2-(1-tert-butoxycarbonyl-1-methylethoxyimino)acetamido]-3-[N,N-dimethyl-N-{2-(5-hydroxy-4-oxo-1,4-dihydropyridin-2-yl)ethyl}ammonio]methyl-3-cephem-4-carboxylate (syn isomer)

IR (Nujol): 3250 (br), 1770, 1720, 1662, 1608 cm$^{-1}$
NMR (D$_2$O-NaHCO$_3$, δ): 1.50 (15H, s), 2.10 (3H, s), 2.17 (3H, s), 3.0–4.2 (6H, m), 4.6–5.0 (2H, m), 5.36 (1H, d, J=5Hz), 5.83 (1H, d, J=5Hz), 6.50 (1H, s), 6.93 (1H, s), 7.56 (1H, s).

(4) 7β-[2-(2-Aminothiazol-4-yl)-2-(1-tert-butoxycarbonyl-1-methylethoxyimino)acetamido]-3-[N,N-dimethyl-N-{(5-hydroxy-4-oxo-1,4-dihydropyridin-2-yl)methyl}ammonio]methyl-3-cephem-4-carboxylate (syn isomer)

IR (Nujol): 3350 (br), 1775, 1720, 1672, 1608 cm$^{-1}$
NMR (D$_2$O-NaHCO$_3$, δ): 1.45 (9H, s), 1.55 (6H, s), 2.96 (3H, s), 3.05 (3H, s), 3.25–4.2 (4H, m), 4.36 (2H, br. s), 5.35 (1H, d, J=5Hz), 5.85 (1H, d, J=5Hz), 6.72 (1H, s), 6.95 (1H, s), 7.71 (1H, s).

(5) 7β-[2-(5-Amino-1,2,4-thiadiazol-3-yl)-2-methoxyiminoacetamido]-3-[N,N-dimethyl-N-{(5-hydroxy-4-oxo-1,4-dihydropyridin-2-yl)methyl}ammonio]methyl-3-cephem- 4-carboxylate (syn isomer)

IR (Nujol): 3250 (br), 1765, 1650, 1600 cm$^{-1}$ (6) 7β-[2-(5-Amino-1,2,4-thiadiazol-3-yl)-2-(1 -carboxy-1-methylethoxyimino)acetamido]-3-[N,N-dimethyl-N-{(5-hydroxy-4-oxo-1,4-dihydropyridin-2-yl)methyl}ammonio]methyl-3-cephem-4-carboxylate (syn isomer)

IR (Nujol): 3250 (br.), 1770, 1670 (sh), 1600 cm$^{-1}$ (7) 7β-[2-(5-Amino-1,2,4-thiadiazol-3-yl)-2-methoxyiminoacetamido]-3-[1-{2-(5-hydroxy-4-oxo-1,4-dihydropyridin- 2-yl)ethyl}-1-pyrrolidinio]methyl-3-cephem-4-carboxylate (syn isomer)

IR (Nujol): 3300 (br.), 1765, 1663 (sh), 1620 cm$^{-1}$ (8) 7β-[2-(5-Amino-1,2,4-thiadiazol-3-yl)-2-(1 -carboxy-1-methylethoxyimino)acetamido]-3-[1-{2-(5 -hydroxy-4-oxo-1,4-dihydropyridin-2-yl)ethyl}-1-pyrrolidinio]methyl-3-cephem-4-carboxylate (syn isomer)

IR (Nujol): 3300 (br), 1770, 1670–1620 (br.) cm$^{-1}$ (9) 7β-[2-(5-Amino-1,2,4-thiadiazol-3-yl)-2-(1-carboxy-1-methylethoxyimino)acetamido]-3-[N,N-dimethyl-N-{2-(5 -hydroxy-4-oxo-1,4-dihydropyridin-2-yl)ethyl}ammonio]methyl-3-cephem-4-carboxylate (syn isomer)

IR (Nujol): 3300 (br.), 1775, 1670, 1615 cm$^{-1}$

(10) 7β-[2-(5-Amino-1,2,4-thiadiazol-3-yl)-2-methoxyiminoacetamido]-3-[N,N-dimethyl-N-{2-(5-hydroxy-4-oxo-1,4-dihydropyridin-2-yl)ethyl}ammonio]methyl-3-cephem- 4-carboxylate (syn isomer)

IR (Nujol): 3250 (br.), 1770, 1670 (sh), 1610 cm$^{-1}$

(11) 7β-[2-(2-Aminothiazol-4-yl)-2-carboxymethoxyiminoacetamido]-3-[N,N-dimethyl-N-{(5-hydroxy-4-oxo-1,4 -dihydropyridin-2-yl)methyl}ammonio]methyl-3-cephem-4-carboxylate (syn isomer)

IR (Nujol): 3250 (br.), 1770, 1662 (sh), 1600 cm$^{-1}$

(12) 7β-[2-(2-Aminothiazol-4-yl)-2-(1-carboxy-1-methylethoxyimino)acetamido]-3-[N,N-dimethyl-N-{2-(5-hydroxy- 4-oxo-1,4-dihydropyridin-2-yl)ethyl}ammonio]methyl-3 -cephem-4-carboxylate (syn isomer)

IR (Nujol): 3250 (br.), 1770, 1665, 1610 cm$^{-1}$

(13) 7β-[2-(2-Aminothiazol-4-yl)-2-(1-carboxy-1-methylethoxyimino)acetamido]-3-[N,N-dimethyl-N-{(5-hydroxy- 4-oxo-1,4-dihydropyridin-2-yl)methyl}ammonio]methyl-3 -cephem-4-carboxylate (syn isomer)

IR (Nujol): 3250, 1770, 1662, 1607 cm$^{-1}$

EXAMPLE 4

(1)

To a suspension of 7β-[2-(2-aminothiazol-4-yl)-2 -tert-butoxycarbonylmethoxyiminoacetamido]-3-[N,N-dimethyl-N-{(5-hydroxy-4-oxo-1,4-dihydropyridin-2-yl)methyl}ammonio]methyl-3-cephem-4-carboxylate (syn isomer) (0.54 g) in anisole (2 ml) was dropwise added trifluoroacetic acid (8 ml) under ice-cooling with stirring. After being stirred at ambient temperature, the mixture was poured into diisopropyl ether (100 ml). The resulting precipitate was collected by filtration, washed with diisopropyl ether and dried under reduced pressure. The precipitate was dissolved in water (30 ml) at pH 7.0 and acidified to pH 1.0 with 6N hydrochloric acid. After removal of precipitated materials, the aqueous solution was subjected to column chromatography on Diaion HP-20 (50 ml). The column was washed with water and the elution was carried out with 30% aqueous methanol. The active fractions were collected and lyophilized to give 7β-[2-(2-aminothiazol-4-yl)-2-carboxymethoxyiminoacetamido]-3-[N,N-dimethyl-N-{(5 -hydroxy-4-oxo-1,4-dihydropyridin-2-yl)methyl}ammonio]methyl-3-cephem-4-carboxylate (syn isomer) (0.28 g).

IR (Nujol): 3250 (br), 1770, 1662 (sh), 1600 cm$^{-1}$
NMR (D$_2$O-NaHCO$_3$, δ): 3.00 (3H, s), 3.07 (3H, s), 3.40, 3.94 (2H, ABq, J=18Hz), 4.1–5.1 (4H, m), 4.45 (2H, br. s), 4.60 (2H, s), 5.35 (1H, d, J=5Hz), 5.86 (1H, d, J=5Hz), 6.75 (1H, s), 6.93 (1H, s), 7.70 (1H, s).

The following compounds were obtained according to a similar manner to that of Example 4 (1).

(2) 7β-[2-(2-Aminothiazol-4-yl)-2-(1-carboxy-1-methylethoxyimino)acetamido]-3-[N,N-dimethyl-N-{2-(5 -hydroxy-4-oxo-1,4-dihydropyridin-2-yl)ethyl}ammonio]methyl-3-cephem-4-carboxylate (syn isomer)

IR (Nujol): 3250 (br.), 1770, 1665, 1610 cm$^{-1}$
NMR (D$_2$O-NaHCO$_3$, δ): 1.50 (6H, s), 3.10 (3H, s), 3.17 (3H, s), 3.0–4.2 (6H, m), 4.6–5.0 (2H, m), 5.35 (1H, d, J=5Hz), 5.81 (1H, d, J=5Hz), 6.50 (1H, s), 6.91 (1H, s), 7.55 (1H, s).

(3) 7β-[2-(2-Aminothiazol-4-yl)-2-(1-carboxy-1-methylethoxyimino)acetamido]-3-[N,N-dimethyl-N-{(5 -hydroxy-4-oxo-1,4-dihydropyridin-2-yl)methyl}ammonio]methyl-3-cephem-4-carboxylate (syn isomer)

IR (Nujol): 21250, 1770, 1662, 1607 cm$^{-1}$
NMR (D$_2$O-NaHCO$_3$, δ): 1.50 (8H, s), 2.98 (3H, s), 3.70 (3H, s), 3.25–4.25 (4H, m), 4.42 (2H, br. s), 5.34 (1H, d, J=5Hz), 5.83 (1H, d, J=5Hz), 6.74 (1H, s), 6.90 (1H, s), 7.72 (1H, s).

(4) 7β-[2-(5-Amino-1,2,4-thiadiazol-3-yl)-2-(1-carboxy-1-methylethoxyimino)acetamido]-3-[N,N-dimethyl-N-{(5-hydroxy-4-oxo-1,4-dihydropyridin-2-yl)methyl}ammonio]methyl-3-cephem-4-carboxylate (syn isomer)

IR (Nujol): 3250 (br.), 1770, 1670 (sh), 1600 cm$^{-1}$ (5) 7β-[2-(5-Amino-1,2,4-thiadiazol-3-yl)-2-(1-carboxy-1-methylethoxyimino)acetamido]-3-[1-{2-(5-hydroxy-4-oxo-1,4-dihydropyridin-2-yl)ethyl}-1-pyrrolidinio]]methyl-3-cephem-4-carboxylate (syn isomer)

IR (Nujol): 3.300 (br.), 1770, 1670–1620 (br.)

(6) 7β-[2-(5-Amino-1,2,4-thiadiazol-3-yl)-2-(1-carboxy-1-methylethoxyimino)acetamido]-3-[N,N-dimethyl-N-{2-(5-hydroxy-4-oxo-1,4-dihydropyridin-2-yl)ethyl}ammonio]methyl-3-cephem-4-carboxylate (syn isomer)

IR (Nujol): 3300 (br.), 1775, 1670, 1615 cm$^{-1}$

Preparation 6

To a suspension of 5-benzyloxy-2-hydroxymethyl-4-pyridone (33 g) in benzene (500 ml) was added thionyl chloride (28.4 ml) at ambient temperature under stirring. After being stirred at the same temperature for 30 minutes, the mixture was refluxed for 4 hours. The resulting mixture was cooled to ambient temperature. The precipitate was collected by filtration, washed with benzene and dried under reduced pressure to give 5-benzyloxy-2-chloromethyl-4-pyridone (41.5 g).

IR (Nujol): 1608, 1585 cm$^{-1}$

NMR (DMSO-d$_6$, δ): 5.00 (2H, s), 5.30 (2H, s), 7.4 (5H, m), 7.56 (1H, s), 8.43 (1H, s)

Preparation 7

A suspension of benzhydryl 7β-amino-3-chloromethyl-3-cephem-4-carboxylate hydrochloride (36.11 g) in a mixture of ethyl acetate (900 ml) and cold water (360 ml) was adjusted to pH 7 with a saturated aqueous solution of potassium carbonate. The separated organic layer was washed with brine, dried over magnesium sulfate and evaporated in vacuo. The residue was pulverized with diisopropyl ether to give the powder (34.40 g). The powder (34.40 g) was added portionwise at 5° C. to acetic formic anhydride prepared from formic acid (15.27 g) and acetic anhydride (33.89 g). The mixture was warmed to room temperature and stirred for 1.8 hours at the same temperature. The mixture was poured into a mixture of ethyl acetate (1 l) and cold water (400 ml) and adjusted to pH 7 with 20% aqueous sodium hydroxide solution under cooling. The separated organic layer was washed with water and brine, dried over magnesium sulfate and concentrated to 100 ml. The residual solution was poured into a mixture of diisopropyl ether (1 l) and hexane (1 l) and the resulting precipitates were collected by filtration to give benzhydryl 7β-formamido-3-chloromethyl-3-cephem-4-carboxylate (29.07 g).

IR (Nujol): 1780, 1720, 1675 cm$^{-1}$

NMR (DMSO-d$_6$, δ): 3.55 and 3.79 (2H, ABq, J=18Hz), 4.53 (2H, s), 5.23 (1H, d, J=5Hz), 5.89 (1H, dd, J=8 and 5Hz), 6.96 (1H, s), 7.2–7.6 (10H, m), 8.15 (1H, s), 9.10 (1H, d, J=8Hz).

Preparation 8

To a solution of benzhydryl 7β-formamido-3-chloromethyl-3-cephem-4-carboxylate (27.34 g) in a mixture of dichloromethane (137 ml) and anisole (27 ml) was added dropwise trifluoroacetic acid (54 ml) and the mixture was stirred at 5° C. for 1.2 hours. The mixture was added dropwise to a cooled mixture of diisopropyl ether (2 l) and hexane (2 l) and the resulting precipitates were collected by filtration, washed with a mixture of diisopropyl ether and hexane (2 l) to give 7β-formamido-3-chloromethyl-3-cephem-4-carboxylic acid (14.03 g).

IR (Nujol): 1775, 1665, 1520 cm$^{-1}$

NMR (DMSO-d$_6$, δ): 3.49 and 3.74 (2H, ABq, J=18Hz), 4.55 (2H, s), 5.15 (1H, d, J=5Hz), 5.78 (1H, dd, J=8 and 5Hz), 8.12 (1H, s), 9.06 (1H, d, J=8Hz).

Preparation 9

2-(N,N-Dimethylamino) methyl-5-hydroxy-4-pyridone (15.85 g) was dissolved in N,N-dimethylformamide (238 ml) by addition of sodium 2-ethylhexanoate (10.44 g). To the resulting solution was added dropwise a cooled solution of 7β-formamido-3-chloromethyl-3-cephem-4-carboxylic acid (13.04 g) at 50C and the mixture was stirred for 2 hours at the same temperature. The mixture was added dropwise to a mixture of ethyl acetate (2.5 l) and diisopropyl ether (2.5 l) and the resulting precipitates were collected by filtration, washed three times with a mixture of ethyl acetate and diisopropyl ether (1:1) and dried in vacuo. The powder was poured into cold water (300 ml) and the mixture was adjusted to pH 3.0 with 1N hydrochloric acid. After the insoluble materials were filtered off, the filtrate was chromatographed on Diaion HP-20 (1300 ml) at 50° C. and the elution was carried out with 10% aqueous isopropyl alcohol. The eluate was lyophilized to give 7β-formamido-3-[N,N-dimethyl-N-{(5-hydroxy-4-oxo-1,4-dihydropyridin-2-yl)methyl}ammonio]methyl-3-cephem-4-carboxylate (8.31 g).

IR (Nujol): 1775, 1670, 1610, 1565, 1515 cm$^{-1}$

NMR (D$_2$O, δ): 3.05 and 3.14 (6H, s x 2), 3.47 and 3.99 (2H, ABq, J=18Hz), 4.45–4.55 (2H, m), 4.40 and 4.90 (2H, ABq, J=14Hz), 5.31 (1H, d, J=5Hz), 5.80 (1H, d, J=5Hz), 6.84 (1H, s), 7.81 (1H, s), 8.24 (1H, s).

Preparation 10

To a cooled suspension of 7β-formamido-3-[N,N-dimethyl-N-{(5-hydroxy-4-oxo-1,4-dihydropyridin-2-yl)methyl}ammonio]methyl-3-cephem-4-carboxylate (1.225 g) in methanol (12 ml) was added dropwise conc. hydrochloric acid (0.83 ml) at 10° C. The mixture was warmed to room temperature and stirred for 2.5 hours. The mixture was poured into ethyl acetate (300 ml) and the precipitates were collected by filtration, washed with ethyl acetate and diisopropyl ether and dried in vacuo. The powder was dissolved in cold water (10 ml) and the resulting solution was chromatographed on Diaion HP-20 (10 ml) at 5° C. and the elution was carried out with cold water. To the eluate (24 ml) was added dropwise isopropyl alcohol (12 ml) under cooling and the mixture was allowed to stand overnight in a refrigerator. The resultant crystal was collected by filtration, washed with a cold mixture of isopropyl alcohol and water (10:1) and cold isopropyl alcohol, and dried in vacuo to give β-amino-3-[N,N-dimethyl-N-{(5-hydroxy-4-oxo-1,4 dihydropyridin- 2-yl)methyl}ammonio]methyl-3-cephem-4-carboxylate dihydrochloride (440 mg).

IR (Nujol): 3350, 1810, 1790, 1640, 1520 cm$^{-1}$

NMR (D$_2$O+NaHCO$_3$, δ): 3.04 and 3.14 (6H, s x 2), 3.48 and 3.99 (2H, ABq, J=18Hz), 4.13 and 4.72 (2H, ABq, J=14Hz), 4.45–4.55 (2H, m), 4.94 (1H, d, J=5Hz), 5.29 (1H, d, J=5Hz), 6.85 (1H, s), 7.82 (1H, s).

Preparation 11

To a cooled solution of 7β-formamido-3-[N,N-dimethyl-N-{(5-hydroxy-4-oxo-1,4-dihydropyridin-2-yl)methyl}ammonio]methyl-3-cephem-4-carboxylate (4.084 g) in formic acid (8.1 ml) was added dropwise conc. hydrochloric acid (2.5 ml). The mixture was warmed to room temperature and stirred for 2.5 hours. The mixture was added dropwise to ethyl acetate (400 ml) and the supernatant was decanted. The residual oil was dissolved in methanol (50 ml) and the solution was poured into ethyl acetate (600 ml). The resulting precipitates were collected by filtration, washed with ethyl acetate and diisopropyl ether and dried in vacuo. The powder was dissolved in cold water (28 ml) and chromatographed on Diaion HP-20 (28 ml) at 5° C., and the elution was carried out with water. To the eluate (30 ml) was added dropwise cold isopropyl alcohol (19 ml) under cooling and the mixture was stirred at 5° C. for an hour. The resultant crystal was collected by filtration washed with a cooled mixture of isopropyl alcohol and water (10:1) and cold isopropyl alcohol, and dried in vacuo to give 7β-amino-3-[N,N-dimethyl-N-{(5-hydroxy-4-oxo-1,4-dihydropyridin- 2-yl)methyl}ammonio]methyl-3-cephem-4-carboxylate dihydrochloride (728 mg).

IR (Nujol): 3350, 1810, 1790, 1640, 1520 $cm^{-1}$

NMR ($D_2O+NaHCO_3$, δ): 3.04 and 3.14 (6H, s x 2), 3.48 and 3.99 (2H, ABq, J=18Hz), 4.13 and 4.72 (2H, ABq, J=14Hz), 4.45–4.55 (2H, m), 4.94 (1H, d, J=5Hz), 5.29 (1H, d, J=5Hz), 6.85 (1H, s), 7.82 (1H, s).

EXAMPLE 5

7 β-amino-3-[N,N-dimethyl-N-{(5-hydroxy-4-oxo-1,4-dihydropyridin- 2-yl)methyl}ammonio]methyl-3-cephem-4-carboxylate dihydrochloride (181 mg) was suspended in a mixture of water (7.2 ml) and tetrahydrofuran (3.6 ml) and adjusted to pH 5 with a saturated aqueous solution of sodium bicarbonate. To the resulting solution was added portionwise a solution of 2-(5 -amino-1,2,4-thiadiazol-3-yl)-2-(1-carboxy-1-methylethoxyimino)acetic methanesulfonic anhydride (syn isomer) (169 mg) in tetrahydrofuran (0.5 ml) at 15° C. and the mixture was stirred for an hour at 15° C. and pH 4.0–6.0. After tetrahydrofuran was evaporated in vacuo, water (30 ml) was added to the residue. The aqueous solution was adjusted to pH 1.0 with 1N hydrochloric acid and filtered to remove the insoluble materials. The filtrate was chromatographed on Diaion HP-20 (15 ml) and the elution was carried out with 15% aqueous isopropyl alcohol. The eluate was lyophilized to give 7β-[2-(5-amino-1,2,4-thiadiazol-3-yl)-2-(1-carboxy-1-methylethoxyimino )acetamido]-3-[N,N-dimethyl-N-{(5 -hydroxy-4-oxo-1,4-dihydropyridin-2-yl)methyl}ammonio]methyl- 3-cephem-4-carboxylate (syn isomer) (124 mg).

IR (Nujol): 3250 (br.), 1770, 1670 (sh), 1600 $cm^{-1}$

NMR ($D_2O-NaHCO_3$, δ): 1.56 (6H, s), 3.03 (3H, br s), 3.10 (3H, br s), 3.44, 3.96 (2H, ABq, J=18Hz), 4.1–5.0 (4H, m), 5.37 (1H, d, J=5Hz), 5.88 (1H, d, J=5Hz), 6.76 (1H, s), 7.71 (1H, s).

EXAMPLE 6

7β-Amino-3-[N,N-dimethyl-N-{(5-hydroxy-4-oxo-1,4-dihydropyridin- 2-yl)methyl}ammonio]methyl-3-cephem-4-carboxylate dihydrochloride (181 mg) was suspended in tetrahydrofuran (9.1 ml). To the suspension was added N-(trimethylsilyl)acetamide (788 mg), and the mixture was stirred at 35° C. for 30 minutes and cooled to 5° C. To the resulting solution was added a solution of 2-(5-amino-1,2, 4-thiadiazol-3-yl)-2-(1-carboxy-1-methylethoxyimino)acetic methanesulfonic anhydride (syn isomer) (169 mg) in tetrahydrofuran (0.5 ml). The mixture was warmed to 20° C. and stirred for 1.2 hours. The mixture was poured into ethyl acetate (200 ml) and the resulting precipitates were collected by filtration, washed with ethyl acetate and diisopropyl ether and dried in vacuo. The powder was suspended in water (40 ml) and adjusted to pH 1 with 1N hydrochloric acid. After the insoluble materials were removed by filtration, the filtrate was chromatographed on Diaion HP-20 (15 ml) and the elution was carried out with 15% aqueous isopropyl alcohol. The eluate was lyophilized to give 7β-[2-(5 -amino-1,2,4-thiadiazol-3-yl)-2-(1-carboxy-1-methylethoxyimino)acetamido]-3-[N,N-dimethyl-N-{(5-hydroxy- 4-oxo-1,4-dihydropyridin-2-yl)methyl}ammonio]methyl-3 -cephem-4-carboxylate (syn isomer) (120 mg).

IR (Nujol): 3250 (br), 1770, 1670 (sh), 1600 $cm^{-1}$

Preparation 12

A mixture of 4,5-dihydroxy-2-pyridinecarboxylic acid dihydrate (15.5 g) in acetic anhydride (77.5 ml) was heated at 90°–95° C. for 30 minutes. After the mixture was cooled, the solvent was evaporated in vacuo. To the residue were added acetone (20 ml) and water (10 ml) and the mixture was stirred for 1.5 hours at room temperature. The mixture was evaporated in vacuo to remove acetone. The aqueous residue was extracted with 10 ethyl acetate and the extract was washed with a saturated aqueous solution of sodium chloride, dried over magnesium sulfate, evaporated in vacuo and triturated with diethyl ether to give 4,5-diacetoxy-2-pyridinecarboxylic acid (14.27 g).

IR (Nujol): 1780, 1750, 1700, 1590 $cm^{-1}$

NMR (DMSO-$d_6$, δ): 2.43 (6H, s), 8.15 (1H, s), 8.75 (1H, s).

Preparation 13

To a suspension of phosphorus pentachloride (4.6 g) in methylene chloride (40 ml) was added 4,5-diacetoxy-2-pyridinecarboxylic acid (4.5 g) at −20° C. with stirring. The stirring was continued for an hour at −18°—12° C. To the reaction mixture was add%d diisopropyl ether (80 ml) below 0° C. The resulting precipitates were collected by filtration, washed with diisopropyl ether and dried over phosphorus pentoxide to give 4,5-diacetoxy- 2-pyridinecarbonyl chloride hydrochloride (5.15 g).

IR (Nujol): 1790, 1750, 1615 $cm^{-1}$

Preparation 14

To a solution of N-methylpiperazine (300 mg) in methylene chloride (10 ml) was added dropwise a solution of 3,4-diacetoxybenzoyl chloride (924 mg) in methylene chloride (4 ml) at 0° C., and then triethylamine (364 mg) was added to the mixture.

The mixture was stirred at 0° C. for 20 minutes and at room temperature for 1 hour. Ice water (10 ml) was added to the mixture and the organic layer was separated, washed with water and brine, dried over magnesium sulfate and evaporated in vacuo. The residue was purified by column chromatography on silica gel (20 g) [eluent: chloroform-methanol (25: 1)] to give 1-methyl- 4-(3,4-diacetoxybenzoyl)piperazine (470 mg) as viscous 10 oil.

IR (Nujol): 2950, 2810, 1765, 1630, 1505 $cm^{-1}$

NMR (DMSO-d$_6$, δ): 2.16 (3H, s), 2.26 (6H, s), 2.1–2.4 (4H, m), 3.1–3.6 (4H, m), 7.31 (3H, s).

Preparation 15

To a suspension of 2-methoxycarbonyl-4-hydroxy-5-benzyloxypyridine (18.15 g) in N-methylpiperazine (21.04 g) was heated to 100° C. for 3.5 hours. The resulting viscous solution was cooled to room temperature, diluted with a mixture of chloroform (270 ml) and methanol (30 ml) and subjected to column chromatography on silica gel (800 g). The eluate was evaporated in vacuo and the residue was purified by column chromatography on silica gel (600 g). The pure fractions were evaporated in vacuo and the residue was pulverized with diisopropyl ether to give 1-methyl-4-(4-hydroxy-5-benzyloxy-2-pyridylcarbonyl) piperazine (3.99 g).

IR (Nujol): 1645, 1610, 1540, 1505 cm$^{-1}$

NMR (DMSO-d$_6$, δ): 2.18 (3H, s), 2.30 (4H, m), 3.51 (4H, m), 5.16 (2H, s), 6.88 (1H, s), 7.3–7.6 (5H, m), 8.02 (1H, s).

Preparation 16

To a solution of 1-methyl-4-(3,4-diacetoxybenzoyl)piperazine (295 mg) in methanol (3 ml) was added a saturated potassium carbonate solution in methanol (6 ml) and the mixture was stirred at room temperature for 30 minutes. The mixture was poured into ice water and adjusted to pH 9 with 1N hydrochloric acid. The mixture was extracted several times with a mixture of chloroform and methanol (20:1 V/V) and the organic layer was washed with brine, dried over magnesium sulfate and evaporated in vacuo. The residue was crystallized by addition of ethyl acetate to give 1-methyl-4-(3,4-dihydroxybenzoyl)piperazine (71 mg) as white crystal.

mp: 222°–225° C.

IR (Nujol): 3160, 1590, 1530 cm$^{-1}$

NMR (DMSO-d$_6$, δ): 2.20 (3H, s), 2.2–2.4 (4H, m), 3.3–3.6 (4H, m), 6.6–6.8 (3H, m), 8.7–9.4 (2H, br).

Preparation 17

To a solution of 1-methyl-4-(4-hydroxy-5-benzyloxy-2-pyridylcarbonyl)piperazine (4.71 g) in methanol (300 ml) was added 10% palladium-carbon (2.35 g) in a stream of nitrogen and the mixture was hydrogenated at atmospheric pressure for 20 minutes. After the catalyst was removed by filtration, the filtrate was evaporated to dryness. The residue was recrystallized from methanol to give 1-methyl-4-(4,5-dihydroxy-2-pyridylcarbonyl)piperazine (1.32 g).

mp: 120°–123° C.

IR (Nujol): 1630, 1545 cm$^{-1}$

NMR (D$_2$O, δ): 2.51 (3H, s), 2.85 (4H, m), 3.72 (4H, m), 6.67 (1H, s), 7.71 (1H, s).

Preparation 18

To a solution of benzhydryl 7β-amino-3-chloromethyl-3-cephem-4-carboxylate hydrochloride (22.6 g) and N-trimethylsilylacetamide (25.0 g) in tetrahydrofuran (250 ml) was added 2-(5-amino-1,2,4-thiadiazol-3-yl)-2-carboxymethoxyiminoacetic methanesulfonic anhydride (syn isomer) (19.8 g) at 0°–5° C. under stirring. The stirring was continued for an hour at the same temperature. The reaction mixture was poured into a mixture of ethyl acetate (500 ml) and water (500 ml). The organic layer was separated, washed with water twice and a saturated aqueous solution of sodium chloride, dried over magnesium sulfate and then concentrated in vacuo. To the residue was added diethyl ether and then the resulting precipitates were collected by filtration to give benzhydryl 7β-[2-(5-amino-1,2,4-thiadiazol-3-yl)-2-carboxymethoxyiminoacetamido]- 3-chloromethyl-3-cephem-4-carboxylate (syn isomer) (17.2 g).

NMR (DMSO-d$_6$, δ): 3.57, 3.70 (2H, ABq, J=18Hz), 4.42 (2H, s), 4.63 (2H, s), 5.22 (1H, d, J=5Hz), 5.90 (1H, dd, J=5Hz, J=8Hz), 6.92 (1H, s), 7.17–7.53 (5H, m), 8.07 (2H, br s), 9.52 (1H, d, J=8Hz).

Preparation 19

To a solution of trifluoroacetic acid (20 ml) and anisole (10 ml) in methylene chloride (50 ml) was added benzhydryl 7β-[2-(5-amino-1,2,4-thiadiazol-3-yl)-2 -carboxymethoxyiminoacetamido]-3-chloromethyl-3-cephem- 4-carboxylate (syn isomer) (7.0 g) at 0°—5° C. under stirring. The stirring was continued for 2 hours at the same temperature. The reaction mixture was poured into a cold mixture of diisopropyl ether (400 ml) and n-hexane (200 ml). The resulting precipitates were collected by filtration to give 7β-[2-(5-amino-1,2,4-thiadiazol- 3-yl)-2-carboxymethoxyiminoacetamido]-3 -chloromethyl-3-cephem-4-carboxylic acid (syn isomer) (5.5 g).

IR (Nujol): 3300, 1770, 1700, 1670, 1610, 1510 cm$^{-1}$

NMR (DMSO-d$_6$, δ): 3.53, 3.73 (2H, ABq, J=18Hz), 4.55 (2H, s), 4.65 (2H, s), 5.17 (1H, d, J=5Hz), 5.83 (1H, dd, J=5Hz, J=8Hz), 8.10 (2H, br s), 9.48 (1H, d, J=8Hz).

Preparation 20

(1)

To a solution of 7β-[2-(5-amino-1,2,4-thiadiazol- 3-yl)-2-carboxymethoxyiminoacetamido]-3-chloromethyl-3 -cephem-4-carboxylic acid (syn isomer) (4.0 g) in N,N-dimethylformamide was added dropwise 1-methyl-4-tert-butoxycarbonylpiperazine (6.7 g) at 20° C. under stirring. The stirring was continued for 1.5 hours at 18°–20° C. The reaction mixture was poured into ethyl acetate (200 ml). The resulting precipitates were collected by filtration to give 7β-[2-(5-amino-1,2,4-thiadiazol-3-yl)- 2-carboxymethoxy iminoacetamido]-3-(1-methyl-4-tert-butoxycarbonyl- 1-piperazinio) methyl-3-cephem-4-carboxylate hydrochloride (syn isomer) (5.71 g).

The following compounds were obtained according to a similar manner to that of Preparation 20 (1).

(2) 7β-[2-(5-amino-1,2,4-thiadiazol-3-yl)-2-ethoxyiminoacetamido]-3-(1-methyl-4-tert-butoxycarbonyl-1-piperazinio)methyl- 3-cephem-4-carboxylate hydrochloride trifluoroacetate (syn isomer)

IR (Nujol): 1770, 1660, 1610, 1520 cm$^{-1}$

NMR (DMSO-d$_6$, δ): 1.26 (3H, t, J=7Hz), 2.9–3.1 (7H, m), 3.3–3.9 (6H, m), 4.10 (2H, q, J=7Hz), 4.8–5.0 (2H, m), 5.18 (1H, d, J=5Hz), 5.76 (1H, dd, J=8 and 5Hz), 8.16 (2H, br s), 9.49 (1H, d, J=8Hz).

(3) 7β-[2-(2-Formamidothiazol-4-yl)-2-tert-butoxycarbonylmethoxyiminoacetamido]-3-(1-methyl-4-tert-butoxycarbonyl- 1-piperazinio) methyl-3-cephem-4-carboxylate hydrochloride (syn isomer)

IR (Nujol): 1780, 1675, 1610, 1540 cm$^{-1}$

NMR (DMSO-d$_6$, δ): 1.43 (18H, s), 3.03 (3H, br s), 3.2–4.3 (10H, m), 4.58 (2H, s), 4.9–5.1 (2H, m), 5.17 (1H, d, J=5Hz), 5.73 (1H, dd, J=8 and J=5Hz), 7.37 (1H, s), 8.47 (1H, s), 9.51 (1H, d, J=8Hz).

Preparation 21

(1)
To a mixture of formic acid (10 ml) and trifluoroacetic acid (5 ml) was added 7β-[2-(5-amino-1,2,4-thiadiazol-3-yl)-2-carboxymethoxyiminoacetamido]-3-(1-methyl-4-tert-butoxycarbonyl-1-piperazinio) methyl-3-cephem-4-carboxylate hydrochloride (syn isomer) (5.7 at 20° C. under stirring. The stirring was continued for 1.5 hours at the same temperature. The reaction mixture was poured into ethyl acetate (200 ml). The resulting precipiates were collected by filtration, added to water. The mixture was adjusted to pH 2.0 with a saturated aqueous solution of sodium bicarbonate and filtered. The filtrate was subjected to column chromatography on Diaion HP-20 using 10% aqueous isopropanol as an eluent. The eluate was evaporated in vacuo to remove isopropanol and then lyophilized to give 7β-[2-(5-amino-1, 2,4-thiadiazol-3-yl)-2-carboxymethoxyiminoacetamido]-3-(1-methyl-1-piperazinio) methyl-3-cephem-4-carboxylate (syn isomer) (1.50 g).

NMR (D$_2$O, δ): 3.20 (3H, s), 5.23 (1H, d, J=5Hz), 5.80 (1H, d, J=5Hz).

The following compound was obtained according to a similar manner to that of Preparation 21(1).

(2) 7β-[2-(5-Amino-1,2,4-thiadiazol-3-yl)-2-ethoxyiminoacetamido]-3-(1-methyl-1-piperazinio)methyl-3-cephem-4-carboxylate (syn isomer)

IR (Nujol): 1765, 1655, 1600, 1510 cm$^{-1}$

NMR (D$_2$O, δ): 1.33 (3H, t, J=7Hz), 3.20 (3H, br s), 3.3–4.8 (6H, m), 4.34 (2H, q, J=7Hz), 4.8–5.0 (2H, m), 5.33 (1H, d, J=5Hz), 5.84 (1H, d, J=5Hz).

Preparation 22

(1) To a solution of 7β-[2-(5-amino-1,2,4-thiadiazol-3-yl)-2-methoxyiminoacetamido]-3-chloromethyl-3-cephem-4-carboxylic acid trifluoroacetate (syn isomer) in N,N-dimethylformamide (150 ml) was added 1-methyl-4-tert-butoxycarbonylpiperazine (30 g). After being stirred at room temperature for 30 minutes, the mixture was added dropwise to ethyl acetate (1.5 l). The resulting precipitate was collected by filtration, washed with ethyl acetate and diisopropyl ether. To a solution of the above precipitate in a mixture of methylene chloride (60 ml) and anisole (20 ml) was added dropwise trifluoroacetic acid (40 ml) under ice-cooling. The reaction mixture was stirred at room temperature for 2 hours and added to diisopropyl ether (1.5 l) under stirring. The resultant precipitate was collected by filtration and dissolved in aqueous sodium bicarbonate, and the solution was adjusted to pH 4.0 with hydrochloric acid and subjected to column chromatography on "Diaion HP-20" (Trademark: prepared by Mitsubishi Chemical Industries) with 5% aqueous isopropyl alcohol as an eluent. The eluate was lyophilized to give 7β-[2-(5-amino-1,2,4-thiadiazol-3-yl)-2-methoxyiminoacetamido]-3-(1-methyl-1-piperazinio)methyl-3-cephem-4-carboxylate (syn isomer) (12.00 g).

IR (Nujol): 3300, 1770, 1670, 1610, 1520 cm$^{-1}$

The following compound was obtained according to a similar manner to that of Preparation 22(1).

(2) 7β-[2-(2-Formamidothiazol-4-yl)-2-methoxyiminoacetamido]-3-(1-methyl-1-piperazinio) methyl-3-cephem-4-carboxylate (syn isomer)

NMR (D$_2$O, δ): 3.12 (3H, s), 3.16–4.30 (10H), 4.03 (3H, s), 5.36 (1H, d, J=5Hz), 5.86 (1H, d, J=5Hz), 7.46 (1H, s), 8.43 (1H, s).

Preparation 23

To a suspension of 7β-[2-(2-formamidothiazol-4-yl)-2-tert-butoxycarbonylmethoxyiminoacetamido]-3-(1-methyl-4-tert-butoxycarbonyl-1-piperazinio)methyl-3-cephem-4-carboxylate hydrochloride (syn isomer) (4.02 g) in methanol (12 ml) was added conc. hydrochloric acid (4.4 ml) at 10° C. The resulting solution was warmed to room temperature and stirred for 4.5 hours. The mixture was pulverized with ethyl acetate (800 ml) and the powder was collected by filtration, washed with ethyl acetate and dried in vacuo. The powder (3.68 g) was suspended in a mixture of dichloromethane (12 ml) and anisole (4 ml), and trifluoroacetic acid (8 ml) was added thereto. After being stirred at room temperature for 3.5 hours, the mixture was pulverized with diisopropyl ether (800 ml) and the powder was collected by filtration and washed with diisopropyl ether. The powder was suspended in a mixture of water (100 ml) and ethyl acetate (30 ml) and adjusted with a saturated aqueous solution of sodium bicarbonate. After removal of the insoluble materials, the aqueous layer was separated, adjusted to pH 4 with 1N hydrochloric acid and chromatographed on Diaion HP-20 (250 ml). The elution was carried out with 10% aqueous isopropyl alcohol. The eluate was lyophilized to give 7β-[2-(2-aminothiazol-4-yl)-2-carboxymethoxyiminoacetamido]-3-(1-methyl-1-piperazinio) methyl-3-cephem-4-carboxylate (syn isomer) (763 mg).

IR (Nujol): 1780, 1720, 1670, 1630 cm$^{-1}$

NMR (D$_2$O+NaHCO$_3$, δ): 3.10 (3H, br s), 3.15–3.6 (6H, m), 4.8–5.0 (2H, m), 4.53 (2H, s), 5.30 (1H, d, J=5Hz), 5.81(1H, d, J=5Hz), 6.98 (1H, s).

EXAMPLE 7

To a solution of 7β-[2-(2-formamidothiazol-4-yl)-2-methoxyiminoacetamido]-3-chloromethyl-3-cephem-4-carboxylic acid (syn isomer) (920 mg) in N,N-dimethylformamide (5 ml) was added 1-methyl-4-(3,4-dihydroxybenzoyl)piperazine (945 mg) at 0° C. and the mixture was stirred at 0° C. for 3.5 hours. The mixture was added dropwise to ethyl acetate (200 ml) under stirring and the pulverized product was collected by filtration and washed with ethyl acetate to give 7β-[2-(2-formamidothiazol-4-yl)-2-methoxyiminoacetamido]-3-[1-methyl-4-(3,4-dihydroxybenzoyl)-1-piperazinio]methyl-3-cephem-4-carboxylate (syn isomer) (1.53 g).

NMR (DMSO-d$_6$, δ): 2.87 (3H, s), 2.9–3.05 (4H, m), 3.6–3.8 (4H, m), 3.87 (3H, s), 5.16 (1H, d, J=5Hz), 5.74 (1H, dd, J=8Hz and 5Hz), 6.7–6.9 (3H, m), 7.35 (1H, s), 8.46 (1H, s), 9.1–9.5 (2H, br), 9.59 (1H, d, J=8Hz), 12.50 (1H, s).

EXAMPLE 8

To a suspension of 1-methyl-4-(4,5-dihydroxy-2-pyridylcarbonyl)piperazine (800 mg) in dimethyl sulfoxide (8 ml) was added sodium 2-ethylhexanoate (840 mg). The solution was added dropwise to a solution of 7β-[2-(5-amino-1,2, 4-thiadiazol-3-yl)-2-allyloxyiminoacetamido]-3-chloromethyl-3-cephem-4-carboxylate trifluoroacetate (syn isomer) (965 mg) in dimethyl sulfoxide (7 ml) at room temperature. After being stirred for 4 hours, the mixture was poured into ethyl acetate (200 ml) and the resulting precipitates were collected by filtration. The precipitates were dissolved in water and then adjusted to pH 3.0 with aqueous sodium bicarbonate. The resulting solution was subjected to column chromatography on Diaion HP-20 using 15% aqueous isopropyl alcohol as an eluent and the objective fraction was 10 lyophilized to give 7β-[2-(5-amino-1,2,4-thiadiazol-3-yl)-2-allyloxyiminoacetamido]-3-[1-methyl-4-(4,5-dihydroxy-2-pyridylcarbonyl)-1-piperazinio]methyl-3-cephem-4-carboxylate (syn isomer) (380 mg).

IR (Nujol): 1770, 1610, 1530, 1650 cm$^{-1}$

NMR (D$_2$O-NaHCO$_3$, δ): 3.16 (3H, s), 3.26–4.40 (10H), 4.78 (2H, d, J=5Hz), 5.26 (1H, d, J=5Hz), 5.13–5.53 (2H, m), 5.85 (1H, dd, J=5Hz, 8Hz), 5.86–6.30 (1H, m), 6.70 (1H, s), 7.70 (1H, s)

EXAMPLE 9

The following compounds were obtained according to similar manners to those of Examples 7 and 8.

(1) 7β-[2-(2-Formamidothiazol-4-yl)-2-tert-butoxycarbonylmethoxyiminoacetamido]-3-[1-methyl-4-(3,4-dihydroxybenzoyl)- 1-piperazinio]methyl-3-cephem-4-carboxylate hydrochloride (syn isomer)

NMR (DMSO-d$_6$, δ): 1.40 (9H, s), 3.10 (3H, br s), 3.20–3.80 (10H), 4.55 (2H, s), 4.90–5.15 (2H, m), 5.18 (1H, d, J=5Hz), 5.68 (1H, dd, J=5Hz, 8Hz), 6.50–6.93 (3H, m), 6.73 (1H, s), 8.48 (1H, s).

(2) 7β-[2-(5-Amino-1,2,4-thiadiazol-3-yl)-2 -ethoxyiminoacetamido]-3-[1-methyl-4-(4,5-dihydroxy-2-pyridylcarbonyl)- 1-piperazinio]methyl-3-cephem-4-carboxylate (syn isomer)

IR (Nujol): 3280, 1770, 1615, 1540 cm$^{-1}$

NMR (DMSO-d$_6$, d): 1.25 (3H, t, J=7Hz), 3.06 (3H, br s), 3.3–3.8 (6H, m), 4.15 (2H, q, J=7Hz), 4.2-and 5.0 (2H, m), 5.08 (1H, d, J=5Hz), 5.66 (1H, dd, J=8 and 5Hz), 7.05 (1H, s), 7.83 (1H, s), 8.04 (2H, br s), 9.41 (1H, d, J=8Hz).

EXAMPLE 10

To a suspension of 7β-[2-(2-formamidothiazol-4-yl)-2-methoxyiminoacetamido]-3-[1-methyl-4-(3,4-dihydroxybenzoyl)- 1-piperazinio]methyl-3-cephem-4-carboxylate (syn isomer) (1.52 g) in methanol (9 ml) was added concentrated hydrochloric acid (1.92 ml). After being stirred at room temperature for 4 hours, the solution was poured into ice water (40 ml) and adjusted to pH 2 with a saturated aqueous solution of sodium bicarbonate. The mixture was concentrated in vacuo to remove methanol. The concentrate was adjusted to pH 2 with a saturated aqueous solution of sodium bicarbonate and subjected to column chromatography on "Diaion HP-20" (40 ml), and the elution was carried out with 40% aqueous isopropyl alcohol. The eluate was concentrated in vacuo and lyophilized to give 7β-[2-(2-aminothiazol- 4-yl)-2-methoxyiminoacetamido]-3-[1-methyl-4-(3,4-dihydroxybenzoyl)- 1-piperazinio]methyl-3-cephem-4-carboxylate (syn isomer) (548 mg).

IR (Nujol): 1775, 1660, 1610, 1525 cm$^{-1}$

NMR (DMSO-d$_6$, d): 3.07 (3H, s), 3.3–3.6 (4H, m), 3.7–4.0 (6H, m), 4.1 and 5.05 (2H, m), 5.11 (1H, d, J=5Hz), 5.65 (1H, dd, J=8 and 5Hz), 6.71 (1H, s), 6.7–6.9 (3H, m), 9.49 (1H, d, J=8Hz).

EXAMPLE 11

The following compounds were obtained according to a similar manner to that of Example 10.

(1) 7β-[2-(2-Aminothiazol-4-yl)-2-methoxyiminoacetamido]- 3-[1-methyl-4-(4,5-dihydroxy-2-pyridylcarbonyl)-1 -piperazinio]methyl-3-cephem-4-carboxylate (syn isomer)

IR (Nujol): 1770, 166 0, 16 10, 1530 cm$^{-1}$

NMR (D$_2$O-NaHCO$_3$, δ): 3.20 (3H, s), 3.30–4.20 (10 H), 4.01 (3H, s), 5.36 (1H, d, J=5Hz), 5.85 (1H, d, J:=5Hz), 6. 73 (1H, s), 6.97 (1H, s), 7.73 (1H, s).

(2) 7β-[2-(2-Aminothiazol-4-yl)-2-tert-butoxycarbonylmethoxyiminoacetamido]-3-[1-methyl-4-(3,4-dihydroxybenzoyl)- 1-piperazinio]methyl-3-cephem-4-carboxylate dihydrochloride (syn isomer)

NMR (DMSO-d$_6$, δ): 1.41 (9H, s), 3.15 (3H, s), 3.20–4.30 (10H), 4.63 (2H, s), 5.33 (1H, d, J=5Hz), 5.88 (1H, dd, J=8Hz, 5Hz), 6.63–6.95 (3H, m), 6.95 (1H, s), 9.80 (1H, d, J=8Hz).

EXAMPLE 12

To a solution of 4,5-dihydroxy-2-pyridinecarboxylic acid (3.1 g) and 1-hydroxybenzotriazole (4.0 g) in dimethyl sulfoxide (30 ml) was added N,N'-dicyclohexylcarbodiimide (6.2 g). After being stirred at room temperature for 1 hour, the reaction mixture was added to a solution of 7β-[2-(5-amino-1,2,4 -thiadiazol-3-yl)-2-methoxyiminoacetamido]-3-(1-methyl- 1-piperazinio)methyl-3-cephem-4-carboxylate (syn isomer) (10.0 g) and N-trimethylsilylacetamide (3.0 g) in dimethyl sulfoxide (50 ml), and the stirring was continued for 30 minutes. The mixture was added dropwise to diisopropyl ether (1.5 l) and the resulting precipitate was collected by filtration, which was dissolved in an aqueous solution of sodium bicarbonate, After the insoluble material was filtered off, the filtrate was adjusted to pH 3.0 with 1N hydrochloric acid and subjected to column chromatography on "Diaion HP-20" with 5% aqueous isopropyl alcohol as an eluent. The eluate was lyophilized to give 7β-[2-(5-amino-1,2,4-thiadiazol- 3-yl)-2-methoxyiminoacetamido]-3-[1-methyl- 4-(4,5-dihydroxy-2-pyridylcarbonyl)-1-piperazinio]methyl-3-cephem-4-carboxylate (syn isomer) (0.5 g).

IR (Nujol): 3300, 1770, 1610 cm$^{-1}$

NMR (DMSO-d$_6$, δ): 3.08 (3H, s), 3.92 (3H, s), 5.12 (1H, d, J=5Hz), 5.70 (1H, dd, J=5, 8Hz), 7.10 (1H, s), 7.89 (1H, s), 8.10 (2H, br s), 9.47 (1H, d, J=8Hz).

EXAMPLE 13

The solution of 7β-[2-(5-amino-1,2,4-thiadiazol-3-yl)-2-carboxymethoxyiminoacetamido]-3-(1-methyl-1-piperazinio)methyl- 3-cephem-4-carboxylate (syn isomer) (540 mg) in acetone (5 ml) and water (5 ml) was adjusted to pH 7.0 with a saturated aqueous solution of sodium bicarbonate. To the mixture was added 3,4-diacetoxybenzoyl chloride (308 mg) at pH 6.5–7.0. The mixture was stirred for an hour and evaporated in vacuo to remove acetone. The residue was adjusted to pH 8.5 with a saturated aqueous solution of sodium bicarbonate and then stirred for 2 hours at room temperature. The mixture was adjusted to pH 3.5 with 3N hydrochloric acid and then filtered. The filtrate was subjected to column chromatography on Diaion HP-20 using 5% aqueous isopropyl alcohol as an eluent. The eluate was evaporated in vacuo to remove isopropyl alcohol and then lyophilized to give 7β-[2-(5-amino-1,2,4-thiadiazol-3-yl)-2-carboxymethoxyiminoacetamido]-3-[1-methyl-4-(3,4 -dihydroxybenzoyl)-1-piperazinio]methyl-3-cephem-4-carboxylate (syn isomer) (265 mg).

IR (Nujol): 3300, 1770, 1600, 1620 cm$^{-1}$

NMR (D$_2$O, δ): 3.15 (3H, br s), 5.32 (1H, d, J=5Hz), 5.85 (1H, d, J=5Hz), 6.90 (3H, br s).

EXAMPLE 14

To a solution of 7β-[2-(5-amino-1,2,4-thiadiazol- 3-yl)-2-ethoxyiminoacetamido]-3-(1-methyl-1-piperazinio)methyl- 3-cephem-4-carboxylate (syn isomer) (255 mg) in a mixture of water (5 ml) and acetone (5 ml) was added 4,5-diacetoxy-2-pyridinecarbonyl chloride hydrochloride (309 mg), with maintaining the pH of the solution to 8.0–8.5 by addition of saturated aqueous sodium bicarbonate. After stirring for 30-minutes, acetone was removed by evaporation in vacuo and the residue was adjusted to pH 8 and stirred for 2 hours. The mixture was adjusted to pH 3.0 with 1N hydrochloric acid and chromatographed on Diaion HP-20 (50 ml), and the elution was carried out with 10% aqueous isopropyl alcohol. The eluate was lyophilized to give 7β-[2-(5-amino-1,2,4 -thiadiazol-3-yl)-2-ethoxyiminoacetamido]-3-[1-methyl-4 (4,5-dihydroxy-2-pyridylcarbonyl)-1-piperazinio]methyl- 3-cephem-4-carboxylate (syn isomer) (155 mg).

IR (Nujol): 3200, 1765, 1610, 1520 cm$^{-1}$

NMR (DMSO-d$_6$, δ): 1.24 (3H, t, J=7Hz), 3.05 (3H, br s), 3.3–3.9 (10H, m), 4.13 (2H, q, J=7Hz), 4.1 and 4.96 (2H, m), 5.09 (1H, d, J=5Hz), 5.67 (1H, dd, J=8 and 5Hz), 7.04 (1H, s), 7.84 (1H, s), 8.03 (2H, br s), 9.43 (1H, d, J=8Hz).

EXAMPLE 15

The following compounds were obtained according to similar manners to those of Examples 13 and 14.

(1) 7β-[2-(2-Formamidothiazol-4-yl)-2-methoxyiminoacetamido]-3-[1-methyl-4-(4,5-dihydroxy-2-pyridylcarbonyl)- 1-piperazinio]methyl-3-cephem-4-carboxylate (syn isomer)

NMR (D$_2$O-NaHCO$_3$, δ): 3.22 (3H, s), 3.30–4.30 (10H), 4.05 (3H, s), 5.38 (1H, d, J=5Hz), 5.86 (1H, d, J=5Hz), 6.73 (1H, s), 7.46 (1H, s), 7.73 (1H, s), 8.53 (1H, s) (2) 7β-[2-(5-Amino-1,2,4-thiadiazol-3-yl)-2-carboxymethoxyiminoacetamido]-3-[1-methyl-4-(4,5 -dihydroxy-2-pyridylcarbonyl]-1-piperazinio]methyl-3 -cephem-4-carboxylate (syn isomer)

IR (Nujol): 3300, 1780, 1660, 1600 cm$^{-1}$

NMR (D$_2$O+NaHCO$_3$, δ): 3.33 (3H, s), 5.35 (1H, d, J=5Hz), 5.88 (1H, d, J=5Hz), 6.73 (1H, s), 7.73 (1H, s).

(3) 7β-[2-(2-Aminothiazol-4-yl)-2-carboxymethoxyiminoacetamido]-3-[1-methyl-4-(4,5-dihydroxy-2-pyridylcarbonyl)- 1-piperazinio]methyl-3-cephem-4-carboxylate (syn isomer)

IR (Nujol): 1770, 1660, 1610, 1525 cm$^{-1}$

NMR (D$_2$O-NaHCO$_3$, δ): 3.16 (3H, s), 3.52 (2H, br s), 3.20–4.30 (8H), 4.50–5.00 (2H+2H, m), 5.32 (1H, d, J=5Hz), 5.85 (1H, d, J=5Hz), 6.70 (1H, s), 6.98 (1H, s), 7.70 (1H, s).

EXAMPLE 16

To a suspension of 7β-[2-(2-aminothiazol-4-yl)-2 -tert-butoxycarbonylmethoxyiminoacetamido]-3-[1-methyl-4-(3,4-dihydroxybenzoyl)-1-piperazinio]methyl-3-cephem-4-carboxylate dihydrochloride (syn isomer) (1.35 g) in dichloromethane (5.4 ml) and anisole (1.3 ml) was added dropwise trifluoroacetic acid (4 ml) at 25° C. The stirring was continued for 3 hours at the same temperature. The reaction mixture was poured into diisopropyl ether and the resulting precipitates were collected by filtration. The precipitates were dissolved in water and then adjusted to pH 3.0 with aqueous sodium bicarbonate. The resulting solution was subjected to column chromatography on Diaion HP-20 using 15% aqueous isopropyl alcohol as an eluent. The object fractions were lyophilized to give 7β-[2-(2-aminothiazol-4-yl)-2 -carboxymethoxyiminoacetamido]-3-[1-methyl-4-(3,4-dihydroxybenzoyl)- 1-piperazinio]methyl-3-cephem-4-carboxylate (syn isomer) (320 mg).

IR (Nujol): 1770, 1660, 1610, 1520 cm$^{-1}$

NMR (D$_2$O-NaHCO$_3$, δ): 3.15 (3H, s), 3.20–4.30 (10H), 4.55 (2H, s), 4.60–5.00 (2H, m), 5.32 (1H, d, J=5Hz), 5.82 (1H, d, J=5Hz), 6.80–7.10 (3H, m), 6.90 (1H, s).

EXAMPLE 17

To 1N hydrochloric acid was added 7β-[2-(5-amino-1,2,4-thiadiazol-3-yl)-2-(1-carboxy-1-methylethoxyimino)acetamido]-3-[N,N-dimethyl-N-{(5-hydroxy-4-oxo-1,4 -dihydropyridin-2-yl)methyl]ammonio]methyl-3-cephem-4 -carboxylate (syn isomer) (2.2 g). The mixture was stirred under ice-cooling for 3 hours. The resulting precipitate was collected by filtration, washed with a small amount of cold water and dried under reduced pressure to give 7β-[2-(5-amino-1,2,4-thiadiazol-3-yl)-2-(1-carboxy-1-methylethoxyimino)acetamido]-3-{N,N-dimethyl-N-{(5 -hydroxy-4-oxo-1,4-dihydropyridin-2-yl)methyl}ammonio]methyl-3-cephem-4-carboxylate hydrochloride (syn isomer) (1.1 g).

IR (Nujol): 3450–3150 (br), 2650, 1770, 1670, 1610 cm$^{-1}$

EXAMPLE 18

To a mixture of water (22 ml) and acetone (22 ml) was added 7β-[2-(5-amino-1,2,4-thiadiazol-3-yl)-2-(1-carboxy-1-methylethoxyimino)acetamido]-3-[N,N-dimethyl-N-{(5-hydroxy- 4-oxo-1,4-dihydropyridin-2-yl)methyl}ammonio] methyl-3 -cephem-4-carboxylate (syn isomer) (2.20 g). To the resulting solution was added 97% sulfuric acid (0,699 g). The solution was stirred for 6.5 hours at 25 to 30° C. The resulting crystals were collected by filtration, washed with a mixture of water (9 ml) and acetone (9 ml) and dried under reduced pressure to give sulfuric acid salt (2.17 g) of 7β-[2-(5-amino-1,2,4-thiadiazol-3-yl)-2-(1 -carboxy-1-methylethoxyimino)acetamido]-3-[N,N-dimethyl-N-{(5-hydroxy-4-oxo-1,4,dihydropyridin-2-yl)methyl}ammonio] methyl-3-cephem-4-carboxylate (syn isomer).

mp: 145 (dec.)

IR (Nujol): 3450–3150 (br), 2650 (br), 1780, 1692, 1615, 1558, 1529cm$^{-1}$

EXAMPLE 19

The following compounds were obtained according to similar manner to those of Examples 5 and 6.

(1) 7β-[2-(5-Amino-1,2,4-thiadiazol-3-yl)-2-methoxyiminoacetamido]-3-[N,N-dimethyl-N-{(5-hydroxy-4-oxo-1,4 -dihydropyridin-2-yl)methyl}ammonio]methyl-3-cephem-4-carboxylate (syn isomer)

IR (Nujol): 3250 (br), 1765, 1650, 1600 cm$^{-1}$ (2) 7β-[2-(2-Formamidothiazol-4-yl)-2-tert-butoxycarbonylmethoxyiminoacetamido]-3-[N,N-dimethyl-N-{(5 -hydroxy-4-oxo-1,4-dihydropyridin-2-yl)methyl}ammonio] methyl-3-cephem-4-carboxylate (syn isomer)

IR (Nujol): 3300 (br), 1780, 1730, 1675, 1613 cm$^{-1}$ (3) 7β-[2-(2-Formamidothiazol-4-yl)-2-methoxyiminoacetamido]-3-[N,N-dimethyl-N-{2-(5-hydroxy-4-oxo-1,4 -dihydropyridin-2-yl)ethyl}ammonio]methyl-3-cephem-4-carboxylate (syn isomer)

IR (Nujol): 3200 (br), 1772, 1670, 1608 cm$^{-1}$ (4) 7β-[2-(5-Amino-1,2,4-thiadiazol-3-yl)-2-methoxyiminoacetamido]-3-[1-{2-(5-hydroxy-4-oxo-1,4-dihydropyridin- 2-yl)ethyl}-1-pyrrolidinio]methyl-3-cephem-4-carboxylate (syn isomer)

IR (Nujol): 3300 (br), 1765, 1663 (sh), 1620 cm$^{-1}$ (5) 7β-[2-(5-Amino-1,2,4-thiadiazol-3-yl)-2-(1-carboxy-1-methylethoxyimino)acetamido]-3-[1-{2-(5-hydroxy-4-oxo-1,4-dihydropyridin-2-yl)ethyl}-1-pyrrolidinio]methyl-3-cephem-4-carboxylate (syn isomer)
IR (Nujol): 3300 (br), 1770, 1670–1620 (br) cm$^{-1}$ (6) 7β-[2-(5-Amino-1,2,4-thiadiazol-3-yl)-2-(1-carboxy-1-methylethoxyimino)acetamido]-3-[N,N-dimethyl-N-{2-(5-hydroxy-4-oxo-1,4-dihydropyridin-2-yl)ethyl}ammonio]methyl-3-cephem-4-carboxylate (syn isomer)
IR (Nujol): 3300 (br), 1775, 1670, 1615 cm$^{-1}$ (7) 7β-[2-(5-Amino-1,:2,4-thiadiazol-3-yl)-2-methoxyiminoacetamido]-3-[N,N.-dimethyl-N-{2-(5-hydroxy-4-oxo-1,4-dihydropyridin-2-yl)ethyl}ammonio]methyl-3-cephem-4-carboxylate (syn isomer)
IR (Nujol): 3250 (br), 1770, 1670 (sh), 1610 cm$^{-1}$ (8) 7β-[2-(2-Formamidothiazol-4-yl)-2-(1-tert-butoxycarbonyl-1-methylethoxyimino)acetamido]-3-[N,N-dimethyl-N-{2-(5-hydroxy-4-oxo-1,4-dihydropyridin-2-yl)ethyl}ammonio]methyl-3-cephem-4-carboxylate (syn isomer)
IR (Nujol): 3200, 1770, 1720, 1685 (sh), 1668, 1605 cm$^{-1}$ (9) 7β-[2-(2-Formamidothiazol-4-yl)-2-(1-tert-butoxycarbonyl-1-methylethoxyimino)acetamido]-3-[N,N-dimethyl-N-{(5-hydroxy-4-oxo-1,4-dihydropyridin-2-yl)methyl}ammonio]methyl-3-cephem-4-carboxylate (syn isomer)
IR (Nujol): 3250, 1780, 1720, 1675, 1611 cm$^{-1}$

(10) 7β-[2-(2-Aminothiazol-4-yl)-2-tert-butoxycarbonylmethoxyiminoacetamido]-3-[N,N-dimethyl-N-{(5-hydroxy-4-oxo-1,4-dihydropyridin-2-yl)methyl}ammonio]methyl-3-cephem-4-carboxylate (syn isomer)
IR (Nujol): 3300 (br), 1750, 1730 (sh), 1667, 1608 cm$^{-1}$

(11) 7β-[2-(2-Aminothiazol-4-yl)-2-methoxyiminoacetamido]-3-{N,N-dimethyl-N-{2-(5-hydroxy-4-oxo-1,4-dihydropyridin-2-yl)ethyl}ammonio]methyl-3-cephem-4-carboxylate (syn isomer)
IR (Nujol): 3250 (br), 1770, 1660, 1705 cm$^{-1}$

(12) 7β-[2-(2-Aminothiazol-4-yl)-2-(1-tert-butoxycarbonyl-1-methylethoxyimino)acetamido]-3-[N,N-dimethyl-N-{2-(5-hydroxy-4-oxo-1,4-dihydropyridin-2-yl)ethyl}ammonio]methyl-3-cephem-4-carboxylate (syn isomer)
IR (Nujol): 3250 (br), 1770, 1720, 1662, 1608 cm$^{-1}$

(13) 7β-[2-(2-Aminothiazol-4-yl)-2-(1-tert-butoxycarbonyl-1-methylethoxyimino)acetamido]-3-[N,N-dimethyl-N-{(5-hydroxy-4-oxo-1,4-dihydropyridin-2-yl)methyl}ammonio]methyl-3-cephem-4-carboxylate (syn isomer)
IR (Nujol): 3350 (br), 1775, 1720, 1672, 1608 cm$^{-1}$

(14) 7β-[2-(2-Aminothiazol-4-yl)-2-carboxymethoxyiminoacetamido]-3-[N,N-dimethyl-N-{(5-hydroxy-4-oxo-1,4-dihydropyridin-2-yl)methyl}ammonio]methyl-3-cephem-4-carboxylate (syn isomer)
IR (Nujol): 3250 (br), 1770, 1662 (sh), 1600 cm$^{-1}$

(15) 7β-[2-(2-Aminothiazol-4-yl)-2-(1-carboxy-1-methylethoxyimino)acetamido]-3-[N,N-dimethyl-N-{2-(5-hydroxy-4-oxo-1,4-dihydropyridin-2-yl)ethyl}ammonio]methyl-3-cephem-4-carboxylate (syn isomer)
IR (Nujol): 3250 (br), 1770, 1665, 1610 cm$^{-1}$

(16) 7β-[2-(2-Aminothiazol-4-yl)-2-(1-carboxy-1-methylethoxyimino)acetamido]-3-[N,N-dimethyl-N-{(5-hydroxy-4-oxo-1,4-dihydropyridin-2-yl)methyl}ammonio]methyl-3-cephem-4-carboxylate (syn isomer)
IR (Nujol): 3250, 1770, 1662, 1607 cm$^{-1}$

(17) 7β-[2-(5-Amino-1,2,4-thiadiazol-3-yl)-2-(1-carboxy-1-methylethoxyimino)acetamido]-3-[N,N-dimethyl-N-{(5-hydroxy-4-oxo-1,4-dihydropyridin-2-yl)methyl)ammonio]methyl-3-cephem-4-carboxylate hydrochloride (syn isomer)
IR (Nujol): 3450–3150 (br), 2650, 1770, 1670, 1610 cm$^{-1}$

(18) Sulfuric acid salt of 7β-[2-(5-amino-1,2,4-thiadiazol-3-yl)-2-(1-carboxy-1-methylethoxyimino)acetamido]-3-[N,N-dimethyl-N-{(5-hydroxy-4-oxo-1,4-dihydropyridin-2-yl)methyl}ammonio]methyl-3-cephem-4-carboxylate (syn isomer)
IR (Nujol): 3450–3150 (br), 2650 (br), 1780, 1692, 1615, 1558, 1529 cm$^{-1}$

(19) 7β-[2-(5-Amino-1,2,4-thiadiazol-3-yl)-2-(1-carboxy-1-methylethoxyimino)acetamido]-3-[1-methyl-4-(4,5-dihydroxy-2-pyridylcarbonyl)-1-piperazinio]methyl-3-cephem-4-carboxylate (syn isomer)
IR (Nujol): 1770 cm$^{-1}$

(20) 7β-[2-(2-Formamidothiazol-4-yl)-2-methoxyiminoacetamido]-3-[1-methyl-4-(3,4-dihydroxybenzoyl)-1-piperazinio]methyl-3-cephem-4-carboxylate (syn isomer)
NMR (DMSO-d$_6$, δ): 2.87 (3H, s), 2.9–3.05 (4H, m), 3.6–3.8 (4H, m), 3.87 (3H, s), 5.16 (1H, d, J=5Hz), 5.74 (1H, dd, J=8Hz and 5Hz), 6.7–6.9 (3H, m), 7.35 (1H, s), 8.46 (1H, s), 9.1–9.5 (2H, br), 9.59 (1H, d, J=8Hz), 12.50 (1H, s).

(21) 7β-[2-(5-Amino-1,2,4-thiadiazol-3-yl)-2-allyloxyiminoacetamido]-3-[1-methyl-4-(4,5-dihydroxy-2-pyridylcarbonyl)-1-piperazinio]methyl-3-cephem-4-carboxylate (syn isomer)
IR (Nujol): 1770, 1610, 1530, 1650 cm$^{-1}$

(22) 7β-[2-(2-Formamidothiazol-4-yl)-2-tert-butoxycarbonylmethoxyiminoacetamido]-3-[1-methyl-4-(3,4-dihydroxybenzoyl)-1-piperazinio]methyl-3-cephem-4-carboxylate hydrochloride (syn isomer)
NMR (DMSO-d$_6$, δ): 1.40 (9H, s), 3.10 (3H, br s), 3.20–3.80 (10H), 4.55 (2H, s), 4.90–5.15 (2H, m), 5.18 (1H, d, J=5Hz), 5.68 (1H, dd, J=5Hz, 8Hz), 6.50–6.93 (3H, m), 6.73 (1H, s), 8.48 (1H, s).

(23) 7β-[2-(5-Amino-1,2,4-thiadiazol-3-yl)-2-ethoxyiminoacetamido]-3-[1-methyl-4-(4,5-dihydroxy-2-pyridylcarbonyl)-1-piperazinio]methyl-3-cephem-4-carboxylate (syn isomer)
IR (Nujol): 3280, 1770, 1615, 1540 cm$^{-1}$

(24) 7β-[2-(2-Aminothiazol-4-yl)-2-methoxyiminoacetamido]-3-[1-methyl-4-(3,4-dihydroxybenzoyl)-1-piperazinio]methyl-3-cephem-4-carboxylate (syn isomer)
IR (Nujol): 1775, 1660, 1610, 1525 cm$^{-1}$

(25) 7β-[2-(2-Aminothiazol-4-yl)-2-methoxyiminoacetamido]-3-[1-methyl-4-(4,5-dihydroxy-2-pyridylcarbonyl)-1-piperazinio]methyl-3-cephem-4-carboxylate (syn isomer)
IR (Nujol): 1770, 1660, 1610, 1530 cm$^{-1}$

(26) 7β-[2-(2-Aminothiazol-4-yl)-2-tert-butoxycarbonylmethoxyiminoacetamido]-3-[1-methyl-4-(3,4-dihydroxybenzoyl)-1-piperazinio]methyl-3-cephem-4-carboxylate dihydrochloride (syn isomer)
NMR (DMSO-d$_6$, δ): 1.41 (9H, s), 3.15 (3H, s), 3.20–4.30 (10H), 4.63 (2H, s), 5.33 (1H, d, J=5Hz), 5.88 (1H, dd, J=8Hz, 5Hz), 6.63–6.95 (3H, m), 6.95 (1H, s), 9.80 (1H, d, J=8Hz).

(27) 7β-[2-(5-Amino-1,2,4-thiadiazol-3-yl)-2-methoxyiminoacetamido]-3-[1-methyl-4-(4,5-dihydroxy-2-pyridylcarbonyl)-1-piperazinio]methyl-3-cephem-4-carboxylate (syn isomer)
IR (Nujol): 3300, 1770, 1610 cm$^{-1}$

(28) 7β-[2-(5-Amino-1,2,4-thiadiazol-3-yl)-2-carboxymethoxyiminoacetamido]-3-[1-methyl-4-(3,4-dihydroxybenzoyl)-1-piperazinio]methyl-3-cephem-4-carboxylate (syn isomer)
IR (Nujol): 3300, 1770, 1600, 1620 cm$^{-1}$

(29) 7β-[2-(2-Formamidothiazol-4-yl)-2-methoxyiminoacetamido]-3-[1-methyl-4-(4,5-dihydroxy-2-pyridylcarbonyl)-1-piperazinio]methyl-3-cephem-4-carboxylate (syn isomer)

NMR (D₂O-NaHCO₃, δ): 3.22 (3H, s), 3.30–4.30 (10H), 4.05 (3H, s), 5.38 (1H, d, J=5Hz), 5.86 (1H, d, J=5Hz), 6.73. (1H, s), 7.46 (1H, s), 7.73 (1H, s), 8.53 (1H, s).

(30) 7β-[2-(5-Amino-1,2,4-thiadiazol-3-yl)-2-carboxymethoxyiminoacetamido]-3-[1-methyl-4-(4,5-dihydroxy-2-pyridylcarbonyl)-1-piperazinio]methyl-3-cephem-4-carboxylate (syn isomer)
IR (Nujol): 3300, 1780, 1660, 1600 cm⁻¹

(31) 7β-[2-(2-Aminothiazol-4-yl)-2-carboxymethoxyiminoacetamido]-3-[1-methyl.-4-(4,5-dihydroxy-2-pyridylcarbonyl)- 1-piperazinio]methyl-3-cephem-4-carboxylate (syn isomer)
IR (Nujol): 1770, 1660, 1610, 1525 cm⁻¹

(32) 7β-[2-(2-Aminothiazol-4-yl)-2-carboxymethoxyiminoacetamido]-3-[1-methyl-4-(3,4-dihydroxybenzoyl)-1-piperazinio]methyl-3-cephem-4-carboxylate (syn isomer)
IR (Nujol): 1770, 1660, 1610, 1520 cm⁻¹

EXAMPLE 20

The following compounds were obtained according to similar manners to those of Examples 7 and 8.

(1) 7β-[2-(5-Amino-1,2,4-thiadiazol-3-yl)-2-(1-carboxy-1-methylethoxyimino)acetamido]-3-[1-methyl-4-(4,5 -dihydroxy-2-pyridylcarbonyl)-1-piperazinio]methyl-3-cephem-4-carboxylate (syn isomer)
IR (Nujol): 1770 cm⁻¹
NMR (D₂O+NaHCO₃, δ): 1.55 (6H, s), 3.16 (3H, s), 3.2–5.1 (12H, m), 5.35 (1H, d, J=5Hz), 5.85 (1H, d, J=5Hz), 6.70 (1H, s), 7.70 (1H, s).

(2) 7β-[2-(2-Aminothiazol-4-yl)-2-methoxyiminoacetamido]- 3-[1-methyl-4-(3,4-dihydroxybenzoyl)-1-piperazinio]methyl- 3-cephem-4-carboxylate (syn isomer)
IR (Nujol): 1775, 1660, 1610, 1.525 cm⁻¹

(3) 7β-[2-(2-Aminothiazol-4-yl)-2-methoxyiminoacetamido]- 3-[1-methyl-4-(4,5-dihydroxy-2-pyridylcarbonyl)-1-piperazinio]methyl-3-cephem-4-carboxylate (syn isomer)
IR (Nujol): 1770, 1660, 1610, 1530 cm⁻¹

(4) 75-[2-(2-Aminothiazol-4-yl)-2-tert-butoxycarbonylmethoxyiminoacetamido]-3-[1-methyl-4-(3,4-dihydroxybenzoyl)- 1-piperazinio]methyl-3-cephem-4-carboxylate dihydrochloride (syn isomer)
NMR (DMSO-d₆, δ): 1.41 (9H, s), 3.15 (3H, s), 3.20–4.30 (10H),4.63 (2H, s), 5.33 (1H, d, J=5Hz), 5.88 (1H, dd, J=8Hz, 5Hz), 6.63–6.95 (3H, m), 6.95 (1H, s), 9.80 (1H, d, J=8Hz).

(5) 7β-[2-(5-Amino-1,2,4-thiadiazol-3-yl)-2-methoxyiminoacetamido]-3-[1-methyl-4-(4,5-dihydroxy-2-pyridylcarbonyl)- 1-piperazinio]methyl-3-cephem-4 -carboxylate (syn isomer)
IR (Nujol): 3300, 1770, 1610 cm⁻¹

(6) 7β-[2-(5-Amino-1,2,4-thiadiazol-3-yl)-2-carboxymethoxyiminoacetamido]-3-[1-methyl-4-(3,4 -dihydroxybenzoyl)-1-piperazinio]methyl-3-cephem-4-carboxylate (syn isomer)
IR (Nujol): 3300, 1770, 1600, 1620 cm⁻¹

(7) 7β-[2-(2-Formamidothiazol-4-yl)-2-methoxyiminoacetamido]-3-[1-methyl-4-(4,5-dihydroxy-2-pyridylcarbonyl)- 1-piperazinio]methyl-3-cephem-4-carboxylate (syn isomer)
NMR (D₂O-NaHCO₃, δ): 3.22 (3H, s), 3.30–4.30 (10H), 4.05 (3H, s), 5.38 (1H, d, J=5Hz), 5.86 (1H, d, J=5Hz), 6.73 (1H, s), 7.46 (1H, s), 7.73 (1H, s), 8.53 (1H, s).

(8) 7β-[2-(5-Amino-1,2,4-thiadiazol-3-yl)-2-carboxymethoxyiminoacetamido]-3-[1-methyl-4-(4,5 -dihydroxy-2-pyridylcarbonyl)-1-piperazinio]methyl-3-cephem-4-carboxylate (syn isomer)
IR (Nujol): 3300, 1780, 1660, 1600 cm⁻¹

(9) 7β-[2-(2-Aminothiazol-4-yl)-2-carboxymethoxyiminoacetamido]-3-[1-methyl-4-(4,5-dihydroxy-2 -pyridylcarbonyl)-1-piperazinio]methyl-3-cephem-4-carboxylate (syn isomer)
IR (Nujol): 1770, 1660, 1610, 1525 cm⁻¹

(10) 7β-[2-(2-Aminothiazol-4-yl)-2-carboxymethoxyiminoacetamido]-3-[1-methyl-4-(3,4-dihydroxybenzoyl)-1-piperazinio]methyl-3-cephem-4-carboxylate (syn isomer)
IR (Nujol): 1770, 1660, 1610, 1520 cm⁻¹

What we claim is:

1. A compound of the formula:

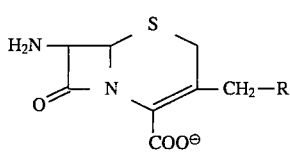

wherein R is a group of the formula:

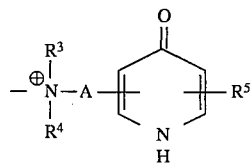

(in which $R^3$ and $R^4$ are each lower alkyl, or $R^3$ and $R^4$ are linked together to form $C_3$–$C_6$ alkylene, A is lower alkylene, and $R^5$ is hydroxy or a protected hydroxy group), or a salt thereof.

2. A compound of claim 1, wherein $R^3$ and $R^4$ are each lower alkyl, $R^5$ is hydroxy and A is lower alkylene.

3. A compound of claim 1, wherein $R^3$ and $R^4$ are each a $C_{1-6}$ alkyl.

4. A compound of claim 1, wherein $R^3$ and $R^4$ are each an alkyl group selected from the group consisting of methyl, ethyl, propyl, isopropyl, butyl, isobutyl, tert -butyl, pentyl, neopentyl, tert-pentyl and hexyl.

5. A compound of claim 1, wherein $R^3$ and $R^4$ are linked together to form an alkylene selected from the group consisting of trimethylene, tetramethylene, pentamethylene and hexamethylene.

6. A compound of claim 1, wherein A is a $C_{1-6}$ alkylene.

7. A compound of claim 1, wherein A is an alkylene selected from the group consisting of methylene, ethylene, trimethylene, tetramethylene, pentamethylene and hexamethylene.

8. A compound of claim 1, wherein $R^5$ is a protected hydroxy group selected from the group consisting of tetrahydropyranyl, formyl, acetyl, propionyl, butyryl, isobutyryl, valeryl, isovaleryl, oxalyl, succinyl, pivaloyl, methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, mesyl, ethanesulfonyl, propanesulfonyl, isopropanesulfonyl, butanesulfonyl, benzenesulfonyl, tosyl, benzoyl, toluoyl, xyloyl, naphthoyl, phthaloyl, indancarbonyl, phenylacetyl, phenylpropionyl, benzoyloxycarbonyl and phenethyloxycarbonyl.

* * * * *